(12) United States Patent
Pitterna

(10) Patent No.: US 7,678,773 B2
(45) Date of Patent: *Mar. 16, 2010

(54) SALTS OF AVERMECTINS SUBSTITUTED IN THE 4″-POSITION AND HAVING PESTICIDAL PROPERTIES

(75) Inventor: Thomas Pitterna, Basel (CH)

(73) Assignee: Merial Limited, Duluth, GA (US)

( * ) Notice: Subject to any disclaimer, the term of this patent is extended or adjusted under 35 U.S.C. 154(b) by 117 days.

This patent is subject to a terminal disclaimer.

(21) Appl. No.: 11/319,687

(22) Filed: Dec. 28, 2005

(65) Prior Publication Data

US 2006/0105971 A1      May 18, 2006

Related U.S. Application Data

(63) Continuation of application No. 10/468,549, filed as application No. PCT/EP02/02044 on Feb. 26, 2002, now abandoned.

(30) Foreign Application Priority Data

Feb. 27, 2001    (CH) ........................................ 373/01

(51) Int. Cl.
   *A61K 31/70* (2006.01)
   *C07H 17/08* (2006.01)
(52) U.S. Cl. ......................................... 514/30; 536/7.1
(58) Field of Classification Search ................ 536/7.1; 514/30
   See application file for complete search history.

(56) References Cited

U.S. PATENT DOCUMENTS

| | | | |
|---|---|---|---|
| 4,203,976 A | | 5/1980 | Fisher et al. |
| 4,206,205 A | | 6/1980 | Mrozik et al. |
| 4,427,663 A | * | 1/1984 | Mrozik .......................... 514/30 |
| 4,622,313 A | | 11/1986 | Wyvrath, Jr. et al. |
| 4,831,016 A | | 5/1989 | Mrozik et al. |
| 4,874,749 A | * | 10/1989 | Mrozik .......................... 514/30 |
| 4,895,837 A | | 1/1990 | Mrozik et al. |
| 5,023,241 A | | 6/1991 | Linn et al. |
| 5,057,499 A | | 10/1991 | Mrozik et al. |

(Continued)

FOREIGN PATENT DOCUMENTS

| | | | |
|---|---|---|---|
| EP | 001688 | | 5/1979 |
| EP | 0089202 | | 9/1983 |
| EP | 0259688 | | 3/1988 |
| EP | 0266131 | | 5/1988 |
| EP | 0301806 | | 1/1989 |
| EP | 0340849 | | 11/1989 |
| EP | 0343708 | | 11/1989 |
| EP | 0375393 A1 | | 6/1990 |
| EP | 0411897 | | 6/1991 |
| EP | 0456509 | | 11/1991 |
| EP | 0 465 121 | * | 1/1992 |
| EP | 0465121 A1 | | 1/1992 |

(Continued)

OTHER PUBLICATIONS

Mrozik et al: "4-Deoxy-4-aminoavermectins with potent broad spectrum antiparasitic activities", Bioorganic & Medical Chem. Lets., vol. 5, No. 20, Oct. 1995, pp. 2435-2440.

(Continued)

*Primary Examiner*—Elli Peselev
(74) *Attorney, Agent, or Firm*—Judy Jarecki-Black; Merial Limited; Thomas Kowalski, Esq.

(57) ABSTRACT

A compound of formula

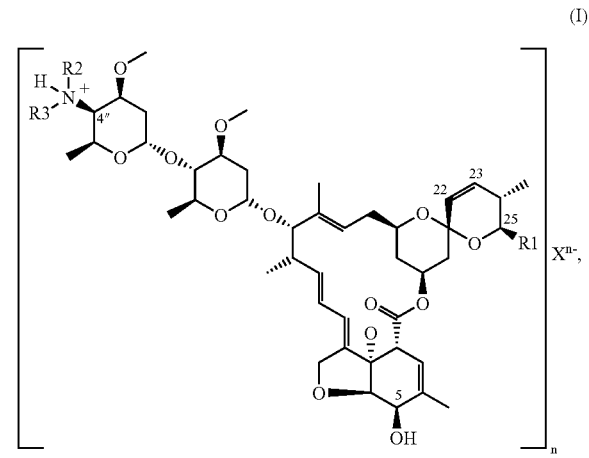

(I)

wherein $X^-$ is an anion;
n is 1, 2, 3 or 4;
$R_1$ is $C_1$-$C_{12}$alkyl, $C_3$-$C_8$cycloalkyl; or $C_2$-$C_{12}$alkenyl;
$R_2$ is hydrogen, unsubstituted or substituted $C_1$-$C_{12}$alkyl or $C_2$-$C_{12}$alkenyl;
$R_3$ is hydrogen, unsubstituted or substituted $C_1$-$C_{12}$alkyl, $C_3$-$C_{12}$cycloalkyl, $C_2$-$C_{12}$alkenyl;
or $C_2$-$C_{12}$alkynyl; or
$R_2$ and $R_3$ together are an alkylene or alkenylene bridge;
and, where applicable, E/Z isomers, E/Z isomeric mixtures and/or tautomers;
with the proviso that $R_1$ is not sec-butyl or isopropyl when $R_2$ is H and $R_3$ is methyl;
and, where applicable, their possible tautomers; a process for the preparation of those compounds and their tautomers and the use thereof; pesticidal compositions in which the active ingredient has been selected from those compounds and their tautomers; and a process for the preparation of those compositions and the use thereof; intermediates, in free form or in salt form, for the preparation of those compounds and, where applicable, their tautomers, in free form or in salt form, are described.

7 Claims, No Drawings

U.S. PATENT DOCUMENTS

| | | | |
|---|---|---|---|
| 5,169,839 | A | 12/1992 | Linn et al. |
| 5,192,546 | A | 3/1993 | Abercrombie et al. |
| 5,208,222 | A | 5/1993 | Meinke et al. |
| 5,229,415 | A | 7/1993 | Linn et al. |
| 5,288,710 | A * | 2/1994 | Cvetovich .............. 514/30 |
| 5,346,698 | A | 9/1994 | Abercrombie et al. |
| 5,362,863 | A | 11/1994 | Cvetovich |
| 5,436,355 | A | 7/1995 | Demchak |
| 5,981,500 | A | 11/1999 | Bishop et al. |
| 6,605,595 | B1 | 8/2003 | Omura et al. |
| 6,875,727 | B2 | 4/2005 | Hofer et al. |
| 6,933,260 | B2 | 8/2005 | Piterna et al. |
| 7,250,402 | B2 | 7/2007 | Omura et al. |
| 7,378,399 | B2 | 5/2008 | Cassayre et al. |
| 2006/0140997 | A1 | 6/2006 | Pitterna et al. |
| 2006/0205595 | A1 | 9/2006 | Pitterna et al. |
| 2008/0051353 | A1 | 2/2008 | Jung et al. |

FOREIGN PATENT DOCUMENTS

| | | |
|---|---|---|
| EP | 0506331 A | 9/1992 |
| EP | 0519731 | 12/1992 |
| EP | 1160252 A | 12/2001 |
| JP | 58-167591 | 10/1983 |
| JP | 05-255342 | 10/1993 |
| JP | 05-306294 | 11/1993 |
| JP | H09-502169 | 3/1997 |
| WO | WO 93/015099 | 8/1993 |
| WO | WO 95/05390 | 2/1995 |
| WO | WO 95/20877 | 8/1995 |
| WO | WO-96-22300 A1 | 7/1996 |
| WO | WO 99/33343 | 7/1999 |
| WO | WO 02/068441 | 9/2002 |
| WO | WO 02/068442 | 9/2002 |
| WO | WO 03/020738 | 3/2003 |
| WO | WO 03/053988 A | 7/2003 |
| WO | WO 04/067534 | 8/2004 |

OTHER PUBLICATIONS

Wrzesinski et al, Journal of Agricultural & Food Chemistry, vol. 44, 1996, pp. 304-312.

Crouch, L. et. al., "Fate of [14C/3H] Emamectin Benzoate in Cabbage. 1. Extractable Residues," Journal of Agricultural and Food Chemistry, (1997), vol. 45, No. 7, p. 2744-2757.

U.S. Appl. No. 10/568,715, filed Feb. 17, 2006, Kasaba et al.
U.S. Appl. No. 10/560,390, filed Mar. 22, 2006, Pitterna et al.
U.S. Appl. No. 10/544,274, filed Aug. 3, 2005, Cassayre et al.
U.S. Appl. No. 10/544,281, filed Aug. 3, 2005, Quaranta et al.
U.S. Appl. No. 10/543,638, filed Jul. 28, 2005, Pitterna et al.
U.S. Appl. No. 10/543,643, filed Apr. 5, 2006, Pitterna et al.
U.S. Appl. No. 10/513,247, filed Nov. 2, 2004, Tobler et al.
U.S. Appl. No. 10/498,858, filed Jun. 14, 2004, Cassayre et al.
U.S. Appl. No. 10/488,225, filed Feb. 26, 2004, Tobler et al.
U.S. Appl. 11/319,686, filed Dec. 28, 2005, Pitterna et al.
U.S. Appl. 10/539,274, filed Mar. 9, 2006, Maienfisch et al.

Cvetovich et al.; J. Org. Chem., 1994, 59, pp. 7704-7708.

Fisher, American Chemical Society Symposium, 1997, vol. 658, Phytochemicals for Pest Control.

J. Med. Chem. 1992, 35, 3879-3884; "Affinity Probes for the Avermectin Bindig Proteins".

Jones, T. K. et al.; "Synthesis and Biological Activity of 4a,4-Disubstituted Avermectins"; Journal of Agriculture and Food Chemistry., American Chemical Society, 42 1994, p. 1786-1790.

Meinke et al. "Synthesis of Avermectin B1-4'-4'a -Oxide: A Precursor to Potent Antihelmintic Agents", Biorganic Medicinal Chemistry Letters, vol. 2, 1992 p. 537.

Mrozik, H. et al.; "Avermectin Acyl Derivatives with Anti-Helmiintic Activity"; Journal of Medicinal Chemistry, vol. 25, 1982, (658-663).

Shoop et al.; Efficacy in Sheep and Pharmacokinetics in CattleThat Led to the Selection of Epinomectin as a Topical Endectocide for Cattle, international Journal for Parasitology, 1996, 26(11), 1227-35.

Yoshua et al.; Simultanious Determination of Residues of Emanectin and Its Metabolites, and Mibimectin. Ivermectin, and Abamectin in Crops by Liquid Chromatography with Fluorescence Detection. Journal of AOAC International vol. 84, No. 3 (910-917).

* cited by examiner

SALTS OF AVERMECTINS SUBSTITUTED IN THE 4"-POSITION AND HAVING PESTICIDAL PROPERTIES

This application is a continuation of U.S. Ser. No. 10/468,549, filed on Aug. 20, 2003 now abandoned, which is a National Stage filing under 35 U.S.C. § 371 of International Application No. PCT/EP02/02044, filed on Feb. 26, 2002.

The invention relates to (1) a compound of formula

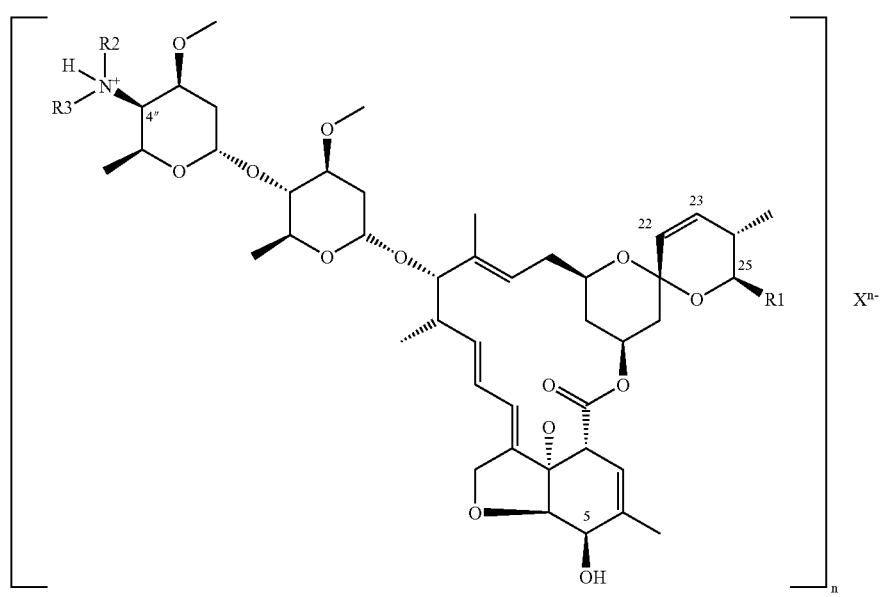

(I)

wherein $X^-$ is an anion;

n is 1, 2, 3 or 4;

$R_1$ is $C_1$-$C_{12}$alkyl, $C_3$-$C_8$cycloalkyl; or $C_2$-$C_{12}$alkenyl;

$R_2$ is hydrogen, unsubstituted or mono- to penta-substituted $C_1$-$C_{12}$alkyl, unsubstituted or mono- to penta-substituted $C_2$-$C_{12}$alkenyl;

$R_3$ is hydrogen, unsubstituted or mono- to penta-substituted $C_1$-$C_{12}$alkyl, unsubstituted or mono- to penta-substituted $C_3$-$C_{12}$cycloalkyl, unsubstituted or mono- to penta-substituted $C_2$-$C_{12}$alkenyl; unsubstituted or mono- to penta-substituted $C_2$-$C_{12}$alkynyl; or $R_2$ and $R_3$ together are a three- to seven-membered alkylene bridge, or a four- to seven-membered alkenylene bridge wherein a —$CH_2$— group may have been replaced by O, S or $NR_4$;

and wherein the substituents of the mentioned alkyl, alkenyl, alkynyl, alkylene, alkenylene and cycloalkyl radicals are selected from the group consisting of OH, halogen, halo-$C_1$-$C_2$alkyl, CN, $NO_2$, $C_2$-$C_6$alkenyl, $C_3$-$C_8$cycloalkyl, norbornylenyl, $C_3$-$C_8$cycloalkenyl; $C_3$-$C_8$cycloalkenyl unsubstituted or substituted by from one to three methyl groups; $C_3$-$C_8$halocycloalkyl, $C_1$-$C_{12}$alkoxy, $C_1$-$C_6$alkoxy-$C_1$-$C_6$alkyl, $C_3$-$C_8$cycloalkoxy, $C_1$-$C_{12}$haloalkoxy, $C_1$-$C_{12}$alkylthio, $C_3$-$C_8$cycloalkylthio, $C_1$-$C_{12}$haloalkylthio, $C_1$-$C_{12}$alkylsulfinyl, $C_3$-$C_8$cycloalkylsulfinyl, $C_1$-$C_{12}$haloalkylsulfinyl, $C_3$-$C_8$halocycloalkylsulfinyl, $C_1$-$C_{12}$alkylsulfonyl, $C_3$-$C_8$cycloalkylsulfonyl, $C_1$-$C_{12}$haloalkylsulfonyl, $C_3$-$C_8$halocycloalkylsulfonyl, $C_2$-$C_8$alkenyl, $C_2$-$C_8$alkynyl, $NH(C_1$-$C_6$alkyl), $N(C_1$-$C_6$alkyl)$_2$, —C(=O)$R_5$, —NHC(=O)$R_6$, —P(=O)(O$C_1$-$C_6$alkyl)$_2$;

aryl, heterocyclyl, aryloxy, heterocyclyloxy; and also aryl, heterocyclyl, aryloxy and heterocyclyloxy that, depending upon the possibilities of substitution at the ring, are mono- to penta-substituted by substituents selected from the group consisting of OH, halogen, CN, $NO_2$, $C_1$-$C_{12}$alkyl, $C_3$-$C_8$cycloalkyl, $C_1$-$C_{12}$haloalkyl, $C_1$-$C_{12}$alkoxy, $C_1$-$C_{12}$haloalkoxy, $C_1$-$C_{12}$alkylthio, $C_1$-$C_{12}$haloalkylthio, $C_1$-$C_6$alkoxy-$C_1$-$C_6$alkyl, dimethylamino-$C_1$-$C_6$alkoxy, $C_2$-$C_8$alkenyl, $C_2$-$C_8$alkynyl, phenoxy, phenyl-$C_1$-$C_6$alkyl; phenoxy unsubstituted or substituted by from one to three substituents selected independently of one another from halogen, methoxy, trifluoromethyl and trifluoromethoxy; phenyl-$C_1$-$C_6$alkoxy unsubstituted or substituted in the aromatic ring by from one to three substituents selected independently of one another from halogen, methoxy, trifluoromethyl and trifluoromethoxy; phenyl-$C_2$-$C_6$alkenyl, phenyl-$C_2$-$C_6$alkynyl, methylenedioxy, —C(=O)$R_5$, —O—C(=O)$R_6$, —NH—C(=O)$R_6$, $NH_2$, $NH(C_1$-$C_{12}$alkyl), $N(C_1$-$C_{12}$alkyl)$_2$, $C_1$-$C_6$alkylsulfinyl, $C_3$-$C_8$cycloalkylsulfinyl, $C_1$-$C_6$haloalkylsulfinyl, $C_3$-$C_8$halocycloalkylsulfinyl, $C_1$-$C_6$alkylsulfonyl, $C_3$-$C_8$cycloalkylsulfonyl, $C_1$-$C_6$haloalkylsulfonyl and $C_3$-$C_8$halocycloalkylsulfonyl;

$R_4$ is $C_1$-$C_8$alkyl, $C_3$-$C_8$cycloalkyl, $C_2$-$C_8$alkenyl, $C_2$-$C_8$alkynyl, benzyl or —C(=O)—$R_5$;

$R_5$ is H, OH, SH, $NH_2$, $NH(C_1$-$C_{12}$alkyl), $N(C_1$-$C_{12}$alkyl)$_2$, $C_1$-$C_{12}$alkyl, $C_1$-$C_{12}$haloalkyl, $C_1$-$C_{12}$alkoxy, $C_1$-$C_{12}$haloalkoxy, $C_1$-$C_6$alkoxy-$C_1$-$C_6$alkoxy, $C_1$-$C_{12}$alkylthio, $C_2$-$C_8$alkenyloxy, $C_2$-$C_8$alkynyloxy; phenyl, phenoxy, benzyloxy, —NH-phenyl, —N($C_1$-$C_6$alkyl)-phenyl, NH—$C_1$-$C_6$alkyl-C(=O)—$R_7$, —N($C_1$-$C_6$alkyl)-$C_1$-$C_6$alkyl-C(=O)—$R_7$; or phenyl, phenoxy, benzyloxy, NH-phenyl or —N($C_1$-$C_6$alkyl)-phenyl substituted in the aromatic ring by from one to three substituents selected independently of one another from halogen, $C_1$-$C_6$alkoxy, $C_1$-$C_6$haloalkyl and $C_1$-$C_6$haloalkoxy;

$R_6$ is H, $C_1$-$C_{12}$alkyl, $C_1$-$C_{12}$haloalkyl, $C_2$-$C_8$alkenyl, $C_2$-$C_8$alkynyl, phenyl, benzyl, $NH_2$, $NH(C_1$-$C_{12}$alkyl), $N(C_1$-$C_{12}$alkyl)$_2$, —NH-phenyl or —N($C_1$-$C_{12}$alkyl)-phenyl; and $R_7$ is H, OH, $C_1$-$C_{12}$alkyl, $C_1$-$C_{12}$alkoxy, $C_1$-$C_6$alkoxy-$C_1$-$C_6$alkoxy, $C_2$-$C_8$alkenyloxy, phenyl, phenoxy, benzyloxy, $NH_2$, $NH(C_1$-$C_{12}$alkyl), $N(C_1$-$C_{12}$alkyl)$_2$, —NH-phenyl or —N($C_1$-$C_{12}$alkyl)-phenyl;

and, where applicable, to E/Z isomers, E/Z isomeric mixtures and/or tautomers;

with the proviso that $R_1$ is not sec-butyl or isopropyl when $R_2$ is H and $R_3$ is methyl;

to a process for the preparation of those compounds and their isomers and tautomers and to the use thereof; to pesticidal compositions in which the active ingredient has been selected from those compounds and their tautomers; and to a method of controlling pests using those compositions.

Certain macrolide compounds are proposed for pest control in the literature, for example in U.S. Pat. No. 4,427,663. The biological properties of those known compounds are not entirely satisfactory, however, for which reason there is a need to provide further compounds having pesticidal properties, especially for the control of insects and members of the order Acarina. That problem is solved according to the invention by the provision of the present compounds of formula (I).

The compounds claimed according to the invention are derivatives of avermectin. Avermectins are known to the person skilled in the art. They are a group of structurally closely related pestidically active compounds which are obtained by fermentation of a strain of the microorganism *Streptomyces avermitilis*. Derivatives of avermectins can be obtained via conventional chemical syntheses.

The avermectins obtainable from Streptomyces avermitilis are designated A1a, A1b, A2a, A2b, B1a, B1b, B2a and B2b. Compounds with the designation "A" have a methoxy radical in the 5-position; those compounds designated "B" have an OH group. The "a" series comprises compounds wherein the substituent $R_1$ (in position 25) is a sec-butyl radical; the "b" series have an isopropyl radical in the 25-position. The number 1 in the name of a compound indicates that atoms 22 and 23 are bonded by a double bond; the number 2 indicates that they are bonded by a single bond and carbon atom 23 carries an OH group. The above designations are retained in the present Application in order in the case of the non-natural avermectin derivatives according to the invention to indicate the specific structural type, which corresponds to natural avermectin. There are claimed according to the invention salts of compounds of the B1 series, more especially mixtures of salts of avermectin derivatives B1a and B1b.

Some of the compounds of formula (I) may be in the form of tautomers. Accordingly, any reference to the compounds of formula (I) hereinabove and hereinbelow is to be understood, where applicable, as including also corresponding tautomers, even if the latter are not specifically mentioned in every case.

The general terms used hereinabove and hereinbelow have the meanings given below, unless defined to the contrary.

Unless defined otherwise, carbon-containing groups and compounds each contain from 1 up to and including 6, preferably from 1 up to and including 4, especially 1 or 2, carbon atoms.

Halogen—as a group per se and as a structural element of other groups and compounds, such as haloalkyl, haloalkoxy and haloalkylthio—is fluorine, chlorine, bromine or iodine, especially fluorine, chlorine or bromine, more especially fluorine or chlorine. In the cases where halogen functions as a leaving group, bromine and iodine are preferred.

Alkyl—as a group per se and as a structural element of other groups and compounds, such as haloalkyl, alkoxy and alkylthio—is, in each case giving due consideration to the number of carbon atoms contained in the group or compound in question, either straight-chained, i.e. methyl, ethyl, propyl, butyl, pentyl, hexyl, heptyl or octyl, or branched, for example isopropyl, isobutyl, sec-butyl, tert-butyl, isopentyl, neopentyl or isohexyl.

Cycloalkyl—as a group per se and as a structural element of other groups and compounds, such as halocycloalkyl, cycloalkoxy and cycloalkylthio—is, in each case giving due consideration to the number of carbon atoms contained in the group or compound in question, cyclopropyl, cyclobutyl, cyclopentyl, cyclohexyl, cycloheptyl or cyclooctyl.

Alkenyl—as a group per se and as a structural element of other groups and compounds—is, in each case giving due consideration to the number of carbon atoms and conjugated or isolated double bonds contained in the group in question, either straight-chained, e.g. allyl, 2-butenyl, 3-pentenyl, 1-hexenyl, 1-heptenyl, 1,3-hexadienyl or 1,3-octadienyl, or branched, e.g. isopropenyl, isobutenyl, isoprenyl, tert-pentenyl, isohexenyl, isoheptenyl or isooctenyl. Alkenyl groups having from 3 to 12, especially from 3 to 6, more especially 3 or 4, carbon atoms are preferred.

Alkynyl—as a group per se and as a structural element of other groups and compounds—is, in each case giving due consideration to the number of carbon atoms and conjugated or isolated double bonds contained in the group or compound in question, either straight-chained, e.g. propargyl, 2-butynyl, 3-pentynyl, 1-hexynyl, 1-heptynyl, 3-hexen-1-ynyl or 1,5-heptadien-3-ynyl, or branched, e.g. 3-methylbut-1-ynyl, 4-ethylpent-1-ynyl, 4-methyl-hex-2-ynyl or 2-methylhept-3-ynyl. Alkynyl groups having from 3 to 12, especially from 3 to 6, more especially 3 or 4, carbon atoms are preferred.

Alkylene and alkenylene are straight-chained or branched bridge members, especially —$CH_2$—$CH_2$—$CH_2$—, —$CH_2$—$CH_2$—$CH_2$—$CH_2$—, —$CH_2$—$CH_2$—$CH_2$—$CH_2$—$CH_2$—, —$CH_2(CH_3)CH_2$—$CH_2$—, —$CH_2C(CH_3)_2$—$CH_2$—, —$CH_2$—CH=CH—$CH_2$— or —$CH_2$—CH=CH—$CH_2$—$CH_2$—.

Halo-substituted carbon-containing groups and compounds, such as haloalkyl, haloalkoxy and haloalkylthio, may be partially halogenated or perhalogenated, the halogen substituents in the case of polyhalogenation being the same or different. Examples of haloalkyl—as a group per se and as a structural element of other groups and compounds, such as haloalkoxy and haloalkylthio—are methyl substituted from one to three times by fluorine, chlorine and/or bromine, such as $CHF_2$ or $CF_3$; ethyl substituted from one to five times by fluorine, chlorine and/or bromine, such as $CH_2CF_3$, $CF_2CF_3$, $CF_2CCl_3$, $CF_2CHCl_2$, $CF_2CHF_2$, $CF_2CFCl_2$, $CF_2CHBr_2$, $CF_2CHClF$, $CF_2CHBrF$ or $CClFCHClF$; propyl or isopropyl substituted from one to seven times by fluorine, chlorine and/or bromine, such as $CH_2CHBrCH_2Br$, $CF_2CHFCF_3$, $CH_2CF_2CF_3$ or $CH(CF_3)_2$; butyl or an isomer thereof substituted from one to nine times by fluorine, chorine and/or bromine, such as $CF(CF_3)CHFCF_3$ or $CH_2(CF_2)_2CF_3$; pentyl or an isomer thereof substituted from one to eleven times by fluorine, chlorine and/or bromine, such as $CF(CF_3)(CHF)_2CF_3$ or $CH_2(CF_2)_3CF_3$; and hexyl or an isomer thereof substituted from one to thirteen times by fluorine, chlorine and/or bromine, such as $(CH_2)_4CHBrCH_2Br$, $CF_2(CHF)_4CF_3$, $CH_2(CF_2)_4CF_3$ or $C(CF_3)_2(CHF)_2CF_3$.

Aryl is especially phenyl, naphthyl, anthracenyl or perylenyl, preferably phenyl.

Heterocyclyl is especially pyridyl, pyrimidyl, s-triazinyl, 1,2,4-triazinyl, thienyl, furyl, tetrahydrofuranyl, pyranyl, tetrahydropyranyl, pyrrolyl, pyrazolyl, imidazolyl, thiazolyl, triazolyl, oxazolyl, thiadiazolyl, oxadiazolyl, benzothienyl, quinolinyl, quinoxalinyl, benzofuranyl, benzimidazolyl, benzopyrrolyl, benzothiazolyl, indolyl, coumarinyl or indazolyl, which are preferably bonded via a carbon atom; preference is given to thienyl, thiazolyl, benzofuranyl, benzothiazolyl, furyl, tetrahydropyranyl and indolyl; especially pyridyl or thiazolyl.

$X^-$ is the anion of an inorganic acid, especially a mineral acid, e.g. sulfuric acid, a phosphoric acid or a hydrohalic acid;

the anion of an organic carboxylic acid, such as an unsubstituted or substituted, e.g. halo-substituted, $C_1$-$C_4$alkanecarboxylic acid, for example acetic acid, a saturated or unsaturated dicarboxylic acid, for example oxalic acid, malonic acid, maleic acid, fumaric acid or phthalic acid, a hydroxycarboxylic acid, for example ascorbic acid, lactic acid, malic acid, tartaric acid or citric acid, or benzoic acid;

the anion of an organic sulfonic acid, such as an unsubstituted or substituted, e.g. halo-substituted, $C_1$-$C_4$alkane- or aryl-sulfonic acid, for example methane- or p-toluene-sulfonic acid;

the anion of an active-H—C compound. Active-H—C compounds include especially organic compounds that carry strongly electron-attracting substituents, such as nitriles, carbonyls or nitro groups. Special preference is given to anions of compounds of formula $Y_1$—$CH_2$—$Y_2$ wherein $Y_1$ and $Y_2$ denote an electron-attracting group. Special preference is given to the anions of malodinitrile, cyanoacetic acid, esters of cyanoacetic acid, amides of cyanoacetic acid, acetoacetic acid, esters of acetoacetic acid, acetylacetone, cyanacetone and barbituric acid; or the anion of an acidic phenol, for example picric acid.

Within the scope of the present invention, special preference is given to (2) compounds according to (1) of formula (I) wherein $R_1$ is isopropyl or sec-butyl, preferably wherein a mixture of the isopropyl and the sec-butyl derivative is present;

(3) compounds according to one of groups (1) and (2) of formula (I) wherein $R_2$ is H;

(4) compounds according to one of groups (1) and (2) of formula (I) wherein $R_2$ is $C_1$-$C_8$alkyl, especially methyl;

(5) compounds according to one of groups (1), (2) and (4) of formula (I) wherein $R_2$ is ethyl;

(6) compounds according to one of groups (1), (2) and (4) of formula (I) wherein $R_2$ is n-propyl;

(7) compounds according to one of groups (1) to (6) of formula (I) wherein $R_3$ is H or unsubstituted or substituted, especially unsubstituted, $C_1$-$C_5$alkyl;

(8) compounds according to one of groups (1) to (7) of formula (I) wherein $R_3$ is methyl;

(9) compounds according to one of groups (1) to (7) of formula (I) wherein $R_3$ is ethyl;

(10) compounds according to one of groups (1) to (7) of formula (I) wherein $R_3$ is n-propyl;

(11) compounds according to one of groups (2) to (7) of formula (I) wherein $R_3$ is isopropyl;

(12) compounds according to one of groups (1) to (7) of formula (I) wherein $R_3$ is n-butyl, sec-butyl, isobutyl or tert-butyl;

(13) compounds according to one of groups (1) to (6) of formula (I) wherein $R_3$ is unsubstituted or substituted, especially unsubstituted, $C_6$-$C_{12}$alkyl;

(14) compounds according to one of groups (1) and (2) of formula (I) wherein $R_2$ and $R_3$ together are —$CH_2$—$CH_2$—$CH_2$— or —$CH_2$—$CH_2$—$CH_2$—$CH_2$—;

(15) compounds according to one of groups (1) and (2) of formula (I) wherein $R_2$ and $R_3$ together are —$CH_2$—$CH_2$—O—$CH_2$—$CH_2$— or —$CH_2$—$CH_2$—N($CH_3$)—$CH_2$—$CH_2$—;

(16) compounds according to one of groups (1) to (6) of formula (I) wherein $R_3$ is substituted $C_1$-$C_4$alkyl and the substituents are selected from the group consisting of OH, halogen, $C_2$-$C_8$alkynyl, $C_3$-$C_8$cycloalkyl; $C_3$-$C_8$cycloalkenyl unsubstituted or substituted by from one to three methyl groups; $C_1$-$C_{12}$alkoxy, —C(=O)$R_5$, —NHC(=O)$R_6$, —P(=O)—(O$C_1$-$C_6$alkyl)$_2$; and phenyl, naphthyl, anthracenyl, phenanthrenyl, fluorenyl, perylenyl and heterocyclyl which are unsubstituted or, depending upon the possibilities of substitution at the ring, mono- to penta-substituted;

especially wherein the substituents of $R_3$ are selected from the group consisting of halogen, $C_3$-$C_8$cycloalkyl, $C_2$-$C_8$alkynyl, —C(=O)$R_5$, —NHC(=O)$R_6$, —P(=O)(O$C_1$-$C_6$alkyl)$_2$; and phenyl, naphthyl, anthracenyl, pyridyl, thiazolyl, imidazolyl, furyl, quinolinyl and pyrazolyl which are unsubstituted or, depending upon the possibilities of substitution at the ring, mono- to tri-substituted;

(17) compounds according to one of groups (1) to (6) of formula (I) wherein $R_3$ is benzyl that carries on the aromatic moiety one to three substituents that are selected from the group consisting of OH, halogen, CN, $NO_2$, $C_1$-$C_2$alkyl, dimethylamino-$C_1$-$C_4$alkoxy, $C_3$-$C_6$cycloalkyl, $C_1$-$C_2$haloalkyl, $C_1$-$C_2$alkoxy, $C_1$-$C_2$haloalkoxy, phenoxy, phenyl-$C_1$-$C_6$alkyl, phenyl-$C_1$-$C_4$alkenyl; phenoxy unsubstituted or substituted by chlorine or methoxy; benzyloxy unsubstituted or substituted by chlorine, methoxy or trifluoromethyl; methylenedioxy, —C(=O)$R_5$, —O—C(=O)$R_6$ and NHC(=O)$R_6$;

$R_5$ is H, OH, $NH_2$, NH($C_1$-$C_2$alkyl), N($C_1$-$C_2$alkyl)$_2$, —O—$C_1$-$C_2$alkyl-C(=O)—$R_7$, NH$C_1$-$C_2$alkyl-C(=O)—$R_7$, $C_1$-$C_6$alkyl, $C_1$-$C_2$alkoxy, $C_1$-$C_2$alkoxy-$C_1$-$C_2$alkoxy, $C_2$-$C_4$alkenyloxy, $C_2$-$C_4$alkynyloxy; phenyl, phenoxy, benzyloxy, NH-phenyl, NH—$C_1$-$C_6$alkyl-C(=O)—$R_7$; or phenyl, phenoxy, benzyloxy or NH-phenyl substituted by halogen, nitro, methoxy, trifluoromethyl or trifluoromethoxy;

$R_6$ is H, $C_1$-$C_3$alkyl, phenyl or benzyl; and $R_7$ is H, OH, $NH_2$, NH($C_1$-$C_{12}$alkyl), N($C_1$-$C_{12}$alkyl)$_2$, $C_1$-$C_{12}$alkyl, $C_1$-$C_{12}$alkoxy, $C_1$-$C_6$alkoxy-$C_1$-$C_6$alkoxy, $C_2$-$C_8$alkenyloxy, phenyl, phenoxy, benzyloxy or NH-phenyl;

(18) compounds according to one of groups (1) to (6) of formula (I) wherein $R_3$ is $C_1$-$C_4$alkyl-C(=O)$R_5$, especially —$CH_2$—C(=O)$R_5$; and $R_5$ is H, OH, $NH_2$, NH($C_1$-$C_2$alkyl), N($C_1$-$C_2$alkyl)$_2$, $C_1$-$C_4$alkyl, $C_1$-$C_{12}$alkoxy, $C_2$-$C_4$alkenyloxy, phenyl, phenoxy, benzyloxy, NH-phenyl, NH—$C_1$-$C_2$alkyl-C(=O)—O—$C_1$-$C_2$-alkyl-phenyl, —P(=O)(O$C_1$-$C_6$alkyl)$_2$; or phenyl, phenoxy, benzyloxy or NH-phenyl substituted by chlorine, fluorine, methoxy, trifluoromethyl or trifluoromethoxy;

more especially wherein $R_5$ is $C_1$-$C_{12}$alkoxy;

(19) compounds according to one of groups (1) to (6) of formula (I) wherein $R_3$ is —$C_2$-$C_6$alkyl-NHC(=O)$R_6$ and $R_6$ is H, $C_1$-$C_4$alkyl, $C_2$-$C_4$alkenyl, $C_2$-$C_4$alkynyl, phenyl or benzyl;

(20) compounds according to one of groups (1) to (6) of formula (I) wherein $R_3$ is —$CH_2$-heterocyclyl, and heterocyclyl denotes pyridyl, furyl, tetrahydrofuranyl, pyranyl, tetrahydropyranyl, pyrazolyl, imidazolyl, thiazolyl, benzothienyl, quinolinyl, quinoxalinyl, benzofuranyl, benzimidazolyl, benzopyrrolyl, benzothiazolyl, indolyl, coumarinyl or indazolyl, the mentioned radicals being unsubstituted or substituted by one or two substituents selected independently of one another from halogen, trifluoromethyl, trifluoromethoxy and nitro; especially pyridyl, furyl, pyrazolyl, imidazolyl, thiazolyl, benzimidazolyl, benzopyrrolyl, benzothiazolyl or indolyl unsubstituted or substituted by one or two substituents selected independently of one another from halogen, trifluoromethyl, trifluoromethoxy and nitro; more especially pyridyl or thiazolyl unsubstituted or substituted by one or two substituents selected independently of one another from halogen, trifluoromethyl, trifluoromethoxy and nitro, especially mono-substituted by chlorine;

(21) compounds according to one of groups (1) to (6) of formula (I) wherein $R_3$ is $C_2$-$C_{10}$alkenyl, especially $C_2$-$C_4$alkenyl, unsubstituted or mono- or di-substituted, especially mono-substituted, by $C_2$-$C_4$alkynyl, —C(=O)—$C_1$-$C_4$alkoxy, —C(=O)—O—$C_1$-$C_4$alkyl-benzoyl, phenyl or halogen; more especially wherein $R_3$ is —$CH_2$—CH=$CH_2$;

(22) compounds according to one of groups (1) to (6) of formula (I) wherein $R_3$ is branched, unsubstituted $C_4$-$C_{10}$alkyl;

(23) compounds according to one of groups (1) to (6) of formula (I) wherein $R_3$ is branched, substituted $C_3$-$C_{10}$alkyl;

(24) compounds according to one of groups (1) to (6) of formula (I) wherein $R_3$ is unsubstituted benzyl;

(25) compounds according to one of groups (1) to (24) of formula (I) wherein $X^{n-}$ is benzoate;

(26) compounds according to one of groups (1) to (24) of formula (I) wherein $X^{n-}$ is a substituted benzoate, especially a mono- or di-substituted benzoate; especially wherein the benzoate is substituted by one or two substituents selected independently of one another from $C_1$-$C_4$alkyl, halo-$C_1$-$C_4$alkyl, OH, SH, halogen and phenyl; more especially mono-substituted by methyl, tert-butyl, trifluoromethyl, OH, SH, fluorine or phenyl;

(27) compounds according to one of groups (1) to (24) of formula (I) wherein $X^{n-}$ is the anion of a sulfonic acid; especially a halo-substituted $C_1$-$C_4$alkane- or aryl-sulfonic acid; more especially trifluoromethylsulfonic acid or benzenesulfonic acid;

(28) compounds according to one of groups (1) to (24) of formula (I) wherein $X^{n-}$ is the anion of a $C_1$-$C_4$alkane- or $C_1$-$C_4$alkene-monocarboxylic acid unsubstituted or substituted by OH, $C_1$-$C_4$alkoxy or phenoxy;

(29) compounds according to one of groups (1) to (24) of formula (I) wherein $X^{n-}$ is the anion of an unsubstituted or substituted dicarboxylic acid; especially tartaric acid, maleic acid or 2,2′-oxydiacetic acid;

(30) compounds according to one of groups (1) to (24) of formula (I) wherein $X^{n-}$ is the anion of an unsubstituted or substituted tricarboxylic acid, especially citric acid;

(31) compounds according to one of groups (1) to (24) of formula (I) wherein $X^{n-}$ is the anion of an acid of the formula Het-COOH wherein Het is a heterocyclic ring; especially wherein Het is furyl;

(32) compounds according to one of groups (1) to (24) of formula (I) wherein $X^{n-}$ is the anion of an inorganic acid, especially sulfate or hydrogen sulfate, more especially sulfate;

(33) compounds according to one of groups (1) to (24), (29) or (30) of formula (I) wherein n is 1 or 2, especially 1.

Special preference within the context of the invention is given to the compounds of formula (I) listed in the Tables and, where applicable, their E/Z isomers and mixtures of E/Z isomers; more especially salts of the compounds 4″-deoxy-4″-epi-amino-avermectin B1;
4″-deoxy-4″-epi-dimethyl-amino-avermectin B1;
4″-deoxy-4″-epi-N-ethylamino-avermectin B1;
4″-deoxy-4″-epi-N-prop-1-ylamino-avermectin B1;
4″-deoxy-4″-epi-(N-ethyl-N-methyl-amino)-avermectin B1;
4″-deoxy-4″-epi-(N-methyl-N-prop-1-yl-amino)-avermectin B1;
4″-deoxy-4″-epi-(N-isopropyl-N-methylamino)-avermectin B1;
4″-deoxy-4″-epi-(N-methyl-N-1-propen-3-yl-amino)-avermectin B1;
4″-deoxy-4″-epi-(N-methyl-N-ethoxycarbonylmethyl-amino)-avermectin B1;
4″-deoxy-4″-epi-(N-methyl-N-benzyl-amino)-avermectin B1;
4″-deoxy-4″-epi-(N-methyl-N-4-difluoromethoxyphenyl-methyl-amino)-avermectin B1;
4″-deoxy-4″-epi-(N-methyl-N-2,5-dichlorophenylmethyl-amino)-avermectin B1;
4″-deoxy-4″-epi-(N-methyl-N-2,5-difluorophenylmethyl-amino)-avermectin B1;
4″-deoxy-4″-epi-(N-methyl-N-2,3,4-trifluorophenylmethyl-amino)-avermectin B1;
4″-deoxy-4″-epi-(pyrrolidin-1-yl)-avermectin B1; and
4″-deoxy-4″-epi-(azetidin-1-yl)-avermectin B1.

The invention relates also to a process for the preparation of the compounds of formula (I) and, where applicable, their tautomers, which process comprises first of all preparing a compound of formula

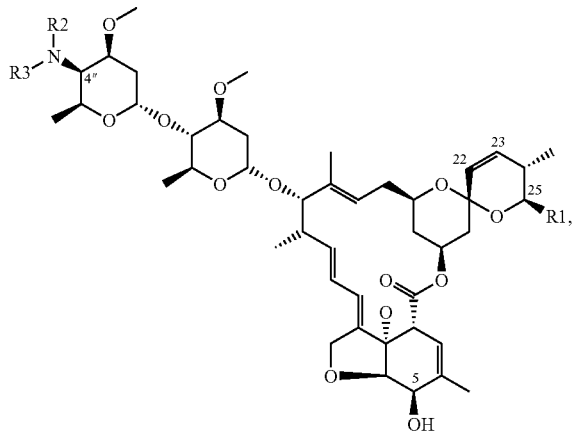

(Ia)

wherein $R_1$, $R_2$ and $R_3$ are as defined for formula (I) above; for example as follows:

(A) for the preparation of a compound of formula (Ia) wherein $R_1$ is as defined above under (1) for formula (I), $R_2$ is hydrogen and $R_3$ is a group $R_{31}$—CH—$R_{32}$, wherein $R_{31}$ is $C_1$-$C_6$alkyl, phenyl, heterocyclyl or unsubstituted or substituted $C_1$-$C_6$alkyl, phenyl or heterocyclyl, and $R_{32}$ is H or unsubstituted or substituted $C_1$-$C_5$alkyl;

a compound of formula (Ia) in which $R_1$ is as defined above under (1) for formula (I) and $R_2$ and $R_3$ are hydrogen and which can be prepared according to methods known per se is reacted in the presence of a reducing agent with a compound $R_{31}$—C(=O)—$R_{32}$, wherein $R_{31}$ and $R_{32}$ are as defined above; or (B) for the preparation of a compound of formula (Ia) wherein $R_1$ and $R_2$ are as defined above under (1) for formula (I), and $R_3$ is as defined above under (1) for formula (I) with the exception of hydrogen, a compound of formula (Ia) in which $R_1$ and $R_2$ are as defined above under (1) for formula (I) and $R_3$ is hydrogen and which can be prepared according to methods known per se, is reacted with a compound of formula $R_3$-Hal wherein $R_3$ is as defined above under (1) for formula (I) and Hal is halogen, especially bromine or iodine; or (C) for the preparation of a compound of formula (Ia) wherein $R_1$ and $R_2$ are as defined above under (1) for formula (I) and $R_3$ is hydroxy-substituted —$CH_2$—$C_1$-$C_{11}$alkyl, a compound of formula (Ia) wherein $R_1$ and $R_2$ are as defined above under (1) for formula (I), $R_3$ is —C(=O)—$R_5$-substituted —$C_1$-$C_{11}$alkyl and $R_5$ is OH or alkoxy is reacted with a reducing agent; or (D) for the preparation of a compound of formula (Ia) wherein $R_1$ and $R_2$ are as defined above under (1) for formula (I) and $R_3$ is COOH-substituted $C_1$-$C_{12}$alkyl, a compound of formula (Ia) wherein $R_1$ and $R_2$ are as defined above under (1) for formula (I), $R_3$ is —C(=O)—$R_5$-substituted $C_1$-$C_{12}$alkyl and $R_5$ is $C_1$-$C_6$alkoxy or benzyloxy is reacted with a base or with a reducing agent; or (E) for the preparation of a compound of formula (Ia) wherein $R_1$ and $R_3$ are as defined above under (1) for formula (I) and $R_2$ is methyl, a compound of formula (Ia) wherein $R_1$ and $R_3$ are as defined above under (1) for formula (I) and $R_2$ is hydrogen is reacted with a compound of the formula methyl-Hal, wherein Hal is a halogen; or with formaldehyde in the presence of a reducing agent; or (F) for the preparation of a compound of formula (Ia) wherein $R_1$ and $R_2$ are as defined above under (1) for formula (I) and $R_3$ is —C(=O)N($R_8$)$_2$-substituted $C_1$-$C_{12}$alkyl and wherein the two $R_8$ are each independently of the other H or unsubstituted or substituted $C_1$-$C_{12}$alkyl, a compound of formula (Ia) wherein $R_1$ and $R_2$ are as defined above under (1) for formula (I) and $R_3$ is —C(=O) $R_5$-substituted $C_1$-$C_{12}$alkyl and $R_5$ is OH is reacted with a compound of formula NH($R_8$)$_2$ wherein $R_8$ is H or unsubstituted or substituted $C_1$-$C_{12}$alkyl, in the presence of a water-removing agent; or (G) for the preparation of a compound of formula (Ia) wherein $R_1$ and $R_2$ are as defined above under (1) for formula (I) and $R_3$ is hydroxy-substituted $C_4$-$C_{12}$alkyl, a compound of formula (Ia) wherein $R_1$ and $R_2$ are as defined above under (1) for formula (I), $R_3$ is —C(=O)—$R_5$-substituted $C_1$-$C_5$alkyl and $R_5$ is $C_1$-$C_{12}$alkoxy is reacted with two moles of a $C_1$-$C_3$alkylmagnesium halide or $C_1$-$C_3$alkyllithium reagent; or (H) for the preparation of a compound of formula (Ia) wherein $R_1$ is as defined above under (1) for formula (I) and $R_2$ and $R_3$ together are a three- to seven-membered alkylene or four- to seven-membered alkenylene bridge, and wherein a $CH_2$ group may have been replaced by O, S or $NR_4$, and $R_4$ is as defined above under (1) for formula (I), a compound of formula (Ia) wherein $R_1$ is as defined above under (1) for formula (I) and $R_2$ and $R_3$ are hydrogen is reacted with a compound of formula Hal-($C_3$-$C_7$alkylene)-Hal or Hal-($C_4$-$C_7$alkenylene)-Hal, wherein Hal is a halogen, and wherein a $CH_2$ group may have been replaced by O, S or $NR_4$, and $R_4$ is as defined above under (1) for formula (I); or (I) for the preparation of a compound of formula (Ia) wherein $R_1$ is as defined above under (1) for formula (I) and $R_2$ and $R_3$ are identical and are as defined under (1) for formula (I), a compound of formula (Ia) wherein $R_1$ is as defined under (1) for formula (I) and $R_2$ and $R_3$ are hydrogen is reacted with two moles of a compound of formula $R_3$-Hal wherein $R_3$ is as defined above for formula (I) and Hal is halogen, preferably bromine or iodine; or (J) for the preparation of a compound of formula (Ia) wherein $R_2$ and $R_3$ are identical and are unsubstituted or mono- to penta-substituted —$CH_2$—$C_1$-$C_{11}$alkyl, unsubstituted or mono- to penta-substituted —$CH_2$—$C_1$-$C_{11}$alkenyl or unsubstituted or mono- to penta-substituted —$CH_2$—$C_1$-$C_{11}$alkynyl, a compound of formula (Ia) wherein $R_1$ is as defined above under (1) for formula (I) and $R_2$ and $R_3$ are hydrogen is reacted with two moles of a compound of formula $R_{31}$—CHO wherein $R_{31}$ is unsubstituted or mono- to penta-substituted $C_1$-$C_{11}$alkyl, unsubstituted or mono- to penta-substituted $C_1$-$C_{11}$alkenyl or unsubstituted or mono- to penta-substituted $C_1$-$C_{11}$alkynyl, in the presence of a reducing agent; and then (K) a compound of formula (Ia) prepared, for example, in accordance with any one of processes A) to J) mentioned above is reacted with an acid $XH_n$ wherein X and n are as defined above under formula (I).

The comments made above in connection with tautomers of compounds of formula (I) apply analogously to the starting materials mentioned hereinabove and hereinbelow in respect of their tautomers.

The reactions described hereinabove and hereinbelow are carried out in a manner known per se, for example in the absence or, customarily, in the presence of a suitable solvent or diluent or of a mixture thereof, the reactions being carried out, as required, with cooling, at room temperature or with heating, for example in a temperature range of approximately from −80° C. to the boiling temperature of the reaction medium, preferably from approximately 0° C. to approximately +150° C., and, if necessary, in a closed vessel, under pressure, under an inert gas atmosphere and/or under anhydrous conditions. Especially advantageous reaction conditions can be found in the Examples.

The reaction time is not critical; a reaction time of from about 0.1 to about 24 hours, especially from about 0.5 to about 10 hours, is preferred.

The product is isolated by customary methods, for example by means of filtration, crystallisation, distillation or chromatography, or any suitable combination of such methods.

The starting materials mentioned hereinabove and hereinbelow that are used for the preparation of the compounds of formula (I) and, where applicable, their tautomers are known or can be prepared by methods known per se, e.g. as indicated below.

Process Variant (A):

Examples of solvents and diluents include: aromatic, aliphatic and alicyclic hydrocarbons and halogenated hydrocarbons, such as benzene, toluene, xylene, mesitylene, Tetralin, chlorobenzene, dichlorobenzene, bromobenzene, petroleum ether, hexane, cyclohexane, dichloromethane, trichloromethane, tetrachloromethane, dichloroethane, trichloroethene or tetrachloroethene; ethers, such as diethyl ether, dipropyl ether, diisopropyl ether, dibutyl ether, tert-butyl methyl ether, ethylene glycol monomethyl ether, ethylene glycol monoethyl ether, ethylene glycol dimethyl ether, dimethoxydiethyl ether, tetrahydrofuran or dioxane; alcohols, such as methanol, ethanol, propanol, isopropanol, butanol, ethylene glycol or glycerol; carboxylic acid, such as acetic acid or formic acid; amides, such as N,N-dimethylformamide, N,N-diethylformamide, N,N-dimethylacetamide, N-methylpyrrolidone or hexamethylphosphoric acid triamide; nitriles, such as acetonitrile or propionitrile; and sulfoxides, such as dimethyl sulfoxide; and also water; or mixtures of the mentioned solvents;

especially suitable are ethers, alcohols, water and carboxylic acids, more especially tetrahydrofuran, acetic acid or water.

The reactions are advantageously carried out in a temperature range of from about room temperature to the boiling point of the solvent used; preference being given to reaction at 10 to 30° C.

In a preferred embodiment of Variant (A) the reaction is carried out at room temperature, in tetrahydrofuran in the presence of acetic acid. Especially preferred conditions for the reaction are described in Example P1.1.

Process Variant (B):

Examples of solvents and diluents include: aromatic, aliphatic and alicyclic hydrocarbons and halogenated hydrocarbons and ethers as listed above under Process variant (A); ketones, such as acetone, methyl ethyl ketone or methyl isobutyl ketone; alcohols, such as methanol, ethanol, propanol, isopropanol, butanol, ethylene glycol or glycerol; carboxylic acid esters, such as methyl acetate, ethyl acetate, or esters of benzoic acid; amides as listed above under Process variant (A); nitrites, such as acetonitrile or propionitrile; and sulfoxides, such as dimethyl sulfoxide; and also water; or mixtures of the mentioned solvents;

especially suitable are water, esters of organic acids, halogenated hydrocarbons and aromatic hydrocarbons; more especially two-phase mixtures of such an organic solvent with water.

The reactions are advantageously carried out in a temperature range of approximately from room temperature to the boiling point of the solvent used, preferably from room temperature up to 90° C., especially up to 60° C., and in the presence of a base, preferably an inorganic base, for example sodium hydroxide, potassium hydroxide, sodium carbonate or sodium hydrogen carbonate.

Especially preferred conditions for the reaction are described, for example, in Examples P1.2, P1.3, P2.1 and P2.7.

Process Variant (C):

Examples of solvents and diluents include: aromatic, aliphatic and alicyclic hydrocarbons and halogenated hydrocarbons and ethers, amides and nitrites as listed above under Process variant (A); and sulfoxides, such as dimethyl sulfoxide; or mixtures of the mentioned solvents; ethers and hydrocarbons being especially suitable.

The reactions are advantageously carried out in a temperature range of from 0° C. to the boiling point of the solvent used, preferably from 0° C. to room temperature. Especially preferred conditions for the reaction are described, for example, in Example P2.2.

Process Variant (D):

Suitable solvents include those mentioned under Variant (A); additionally also ketones, such as acetone, methyl ethyl ketone and methyl isobutyl ketone; and carboxylic acids, such as acetic acid or formic acid; carboxylic acid esters, such as methyl acetate, ethyl acetate, or esters of benzoic acid.

The reactions are advantageously carried out in a temperature range of approximately from room temperature to the boiling point of the solvent used, preferably in the presence of an inorganic base, for example lithium hydroxide, sodium hydroxide, potassium hydroxide, sodium carbonate or sodium hydrogen carbonate.

Especially preferred conditions for this Process variant are described, for example, in Example P2.6.

As an alternative it is possible to choose a reaction variant wherein a reducing agent, especially molecular hydrogen, is used, more especially in a mixture of tetrahydrofuran and water as solvent and in the presence of a heavy metal catalyst, especially a Pd catalyst.

Especially preferred conditions for this Process variant are described, for example, in Example P2.5.

Process Variant (E):

Suitable solvents include those mentioned under Variant (B), especially suitable solvents being esters of organic acids, halogenated hydrocarbons and aromatic hydrocarbons; especially two-phase mixtures of an ester with water.

The reactions are advantageously carried out in a temperature range of from 0° C. to the boiling point of the solvent used, preferably from room temperature to 60° C., and in the presence of a base, preferably an inorganic base, for example sodium hydroxide, potassium hydroxide, sodium carbonate or sodium hydrogen carbonate.

Especially preferred conditions for this Process variant are described, for example, in Example P2.3.

In an alternative embodiment, suitable solvents include those mentioned above, preferably ethers, alcohols, water and carboxylic acids, in combination with a hydride, such as a borohydride, especially $NaCNBH_3$.

Especially preferred conditions for this Process variant are described, for example, in Example P2.4.

Process Variant (F):

Examples of solvents and diluents include: aromatic, aliphatic and alicyclic hydrocarbons and halogenated hydrocarbons; ethers, amides and nitrites as listed above under Process variant (A); ketones, such as acetone, methyl ethyl ketone or methyl isobutyl ketone; carboxylic acid esters, such as methyl acetate, ethyl acetate, or esters of benzoic acid; and sulfoxides, such as dimethyl sulfoxide; or mixtures of the mentioned solvents;

especially suitable are esters of organic acids, such as ethyl acetate.

As water-removing agent there are used the customary peptide coupling reagents, especially carbodiimides and hydroxybenzotriazoles.

The reactions are advantageously carried out in a temperature range of from 0° C. to the boiling point of the solvent used, preferably at room temperature.

Especially preferred conditions for the reaction are described, for example, in Example P2.8.

Process Variant (G):

Examples of solvents and diluents include: aromatic, aliphatic and alicyclic hydrocarbons and ethers as listed above under Process variant (A); and sulfoxides, such as dimethyl sulfoxide; or mixtures of the mentioned solvents; ethers, more especially tetrahydrofuran, being especially suitable.

The reactions are advantageously carried out in a temperature range of from 0° C. to the boiling point of the solvent used, preferably from 0° C. to room temperature.

Especially preferred conditions for the reaction are described, for example, in Example P2.10.

Process Variant (H):

Suitable solvents include those mentioned under Variant (B), especially suitable solvents being water, esters of organic acids, halogenated hydrocarbons and aromatic hydrocarbons; especially two-phase mixtures of such an organic solvent with water.

The reactions are advantageously carried out in a temperature range of from 0° C. to the boiling point of the solvent used, preferably from 90° C. to the boiling point of the solvent, and in the presence of a base, preferably an inorganic base, for example sodium hydroxide, potassium hydroxide, sodium carbonate or sodium hydrogen carbonate.

Especially preferred conditions for the reaction are described, for example, in Example P3.2.

Process Variant (I):

Suitable solvents include those mentioned under Variant (B), especially suitable solvents being water, esters of organic acids, halogenated hydrocarbons and aromatic hydrocarbons; especially two-phase mixtures of such an organic solvent with water.

The reactions are advantageously carried out in a temperature range of from 0° C. to the boiling point of the solvent used, preferably from 90° C. to the boiling point, and in the presence of a base, preferably an inorganic base, for example sodium hydroxide, potassium hydroxide, sodium carbonate or sodium hydrogen carbonate.

Especially preferred conditions for the reaction are described, for example, in Example P3.1.

Process Variant (J):

Suitable solvents include those mentioned under Variant (B), especially suitable solvents being water, ethers of organic acids, alcohols and water; especially two-phase mixtures of an ether with water.

The reactions are advantageously carried out in a temperature range of from 0° C. to the boiling point of the solvent used, preferably at room temperature.

Especially preferred conditions for the reaction are described, for example, in Example P3.3.

Process Variant (K):

Especially suitable solvents are listed under Process variant (B); dichloromethane, acetonitrile, ethyl acetate, toluene and dioxane being especially suitable.

The operation is preferably carried out in a temperature range of from 0° C. to the boiling point of the solvent, preferably at from 0° C. to room temperature.

Especially preferred conditions for the reaction are described in Examples P4.1 to P5.5.

The compounds of formula (I) may be in the form of one of the possible isomers or in the form of a mixture thereof, in the form of pure isomers or in the form of an isomeric mixture, i.e. in the form of a racemic mixture; the invention relates both to the pure isomers and to the racemic mixtures and is to be interpreted accordingly hereinabove and hereinbelow, even if stereochemical details are not mentioned specifically in every case.

The racemates can be resolved into the optical antipodes by known methods, for example by recrystallisation from an optically active solvent, by chromatography on chiral adsorbents, for example high pressure liquid chromatography (HPLC) on acetylcellulose, with the aid of suitable microorganisms, by cleavage with specific, immobilised enzymes, or via the formation of inclusion compounds, for example using chiral crown ethers, only one isomer being complexed.

Apart from by separation of corresponding mixtures of isomers, pure optical isomers can be obtained according to the invention also by generally known methods of enantioselective synthesis, for example by carrying out the process according to the invention using starting materials having correspondingly suitable stereochemistry.

In each case it is advantageous to isolate or synthesise the biologically more active isomer, where the individual components have different biological activity.

The compounds of formula (I) may also be obtained in the form of their hydrates and/or may include other solvents, for example solvents which may have been used for the crystallisation of compounds in solid form.

The invention relates to all those embodiments of the process according to which a compound obtainable as starting material or intermediate at any stage of the process is used as starting material and some or all of the remaining steps are carried out or a starting material is used in the form of a derivative or salt and/or its racemates or antipodes or, especially, is formed under the reaction conditions.

In the processes of the present invention it is preferable to use those starting materials and intermediates which result in the compounds of formula (I) that are especially preferred.

The invention relates especially to the preparation processes described in Examples P1.1 to P5.5.

In the area of pest control, the compounds of formula (I) according to the invention are active ingredients exhibiting valuable preventive and/or curative activity with a very advantageous biocidal spectrum and a very broad spectrum, even at low rates of concentration, while being well tolerated by warm-blooded animals, fish and plants. They are, surprisingly, equally suitable for controlling both plant pests and ecto- and endo-parasites in humans and more especially in productive livestock, domestic animals and pets. They are effective against all or individual development stages of normally sensitive animal pests, but also of resistant animal pests, such as insects and representatives of the order Acarina, nematodes, cestodes and trematodes, while at the same time protecting useful organisms. The insecticidal or acaricidal activity of the active ingredients according to the invention may manifest itself directly, i.e. in the mortality of the pests, which occurs immediately or only after some time, for example during moulting, or indirectly, for example in reduced ovi-position and/or hatching rate, good activity corresponding to a mortality of at least 50 to 60%.

The action of the compounds according to the invention and the compositions comprising them against animal pests can be significantly broadened and adapted to the given circumstances by the addition of other insecticides, acaricides or nematicides. Suitable additives include, for example, representatives of the following classes of active ingredient: organophosphorus compounds, nitrophenols and derivatives, formamidines, ureas, carbamates, pyrethroids, chlorinated hydrocarbons and Bacillus thuringiensis preparations.

Examples of especially suitable mixing partners include: azamethiphos; chlorfenvinphos; bupirimate; cypermethrin, cypermethrin high-cis; cyromazine; diafenthiuron; diazinon; dichlorvos; dicrotophos; dicyclanil; fenoxycarb; fluazuron; furathiocarb; isazofos; iodfenphos; kinoprene; lufenuron; methacriphos; methidathion; monocrotophos; phosphamidon; profenofos; diofenolan; a substance obtainable from the Bacillus thuringiensis strain GC91 or from NCTC11821; pymetrozine; bromopropylate; methoprene; disulfoton; quinalphos; taufluvalinate; thiocyclam; thiometon; aldicarb; azinphos-methyl; benfuracarb; bifenthrin; buprofezin; carbofuran; dibutylaminothio; cartap; chlorfluazuron; chlorpyrifos; cyfluthrin; alpha-cypermethrin; zeta-cypermethrin; deltamethrin; diflubenzuron; endosulfan; ethiofencarb; fenitrothion; fenazaquin; fenobucarb; fenvalerate; formothion; methiocarb; heptenophos; imidacloprid; isoprocarb; methamidophos; methomyl; mevinphos; parathion; parathion-methyl; phosalone; pirimicarb; propoxur; teflubenzuron; terbufos; triazamate; abamectin; fenobucarb; tebufenozide; fipronil; beta-cyfluthrin; silafluofen; fenpyroximate; pyridaben; primicarb; pyriproxyfen; pyrimidifen; nematorin; nitenpyram; NI-25, acetamiprid; avermectin $B_1$ (abamectin); an insect-active extract from a plant; a preparation comprising insect-active nematodes; a preparation obtainable from Bacillus subtilis; a preparation comprising insect-active fungi; a preparation comprising insect-active viruses; AC 303 630; acephate; acrinathrin; alanycarb; alphamethrin; amitraz; AZ 60541; azinphos A; azinphos M; azocyclotin; bendiocarb; bensultap; betacyfluthrin; BPMC; brofenprox; bromophos A; bufencarb; butocarboxim; butylpyridaben; cadusafos; carbaryl; carbophenothion; chloethocarb; chlorethoxyfos; chlormephos; cis-res-methrin; clocythrin; clofentezine; cyanophos; cycloprothrin; cyhexatin; demeton M; demeton S; demeton-S-methyl; dichlofenthion; dicliphos; diethion; dimethoate; dimethylvinphos; dioxathion; edifenphos; emamectin; esfenvalerate; ethion; ethofenprox; ethoprophos; etrimphos; fenamiphos; fenbutatin oxide; fenothiocarb; fenpropathrin; fenpyrad; fenthion; fluazinam; flucycloxuron; flucythrinate; flufenoxuron; flufenprox; fonophos; fosthiazate; fubfenprox; HCH; hexaflumuron; hexythiazox; IKI-220; iprobenfos; isofenphos; isoxathion; ivermectin; lambda-cyhalothrin; malathion; mecarbam; mesulfenphos; metaldehyd; metolcarb; milbemectin; moxidectin; naled; NC 184; omethoate; oxamyl; oxydemethon M; oxydeprofos; permethrin; phenthoate; phorate; phosmet; phoxim; pirimiphos M; pirimiphos A; promecarb; propaphos; prothiofos; prothoate; pyrachlophos; pyrada-phenthion; pyresmethrin; pyrethrum; RH 5992; salithion; sebufos; sulfotep; sulprofos; tebufenpyrad; tebupirimphos; tefluthrin; temephos; terbam; tetrachlorvinphos; thiacloprid; thiamethoxam; thiafenox; thiodicarb; thiofanox; thionazin; thuringiensin; tralomethrin; triarathen; triazophos; triazuron; trichlorfon; triflumuron; trimethacarb; vamidothion; xylylcarb; YI 5301/5302; zetamethrin; DPX-MP062; RH-2485; D 2341 or XMC (3,5-xylyl methylcarbamate).

The said animal pests include, for example, those mentioned in European Patent Application EP-A-736 252, page 5, line 55, to page 6, line 55. The pests mentioned therein are therefore included by reference in the subject matter of the present invention.

It is also possible to control pests of the class Nematoda using the compounds according to the invention. Such pests include, for example, root knot nematodes, cyst-forming nematodes and also stem and leaf nematodes;

especially of *Heterodera* spp., e.g. *Heterodera schachtii, Heterodera avenae* and *Heterodera trifolii; Globodera* spp., e.g. *Globodera rostochiensis; Meloidogyne* spp., e.g. *Meloidogyne incognita* and *Meloidogyne javanica; Radopholus* spp., e.g. *Radopholus simiis; Pratylenchus*, e.g. *Pratylenchus neglectans* and *Pratylenchus penetrans; Tylenchulus*, e.g. *Tylenchulus semipenetrans; Longidorus, Trichodorus, Xiphinema, Ditylenchus, Apheenchoides* and *Anguina;* insbesondere *Meloidogyne*, e.g. *Meloidogyne incognita*, and *Heterodera*, e.g. *Heterodera glycines*.

An especially important aspect of the present invention is the use of the compounds of formula (I) according to the invention in the protection of plants against parasitic feeding pests.

The compounds according to the invention can be used to control, i.e. to inhibit or destroy, pests of the mentioned type occurring on plants, especially on useful plants and ornamentals in agriculture, in horticulture and in forestry, or on parts of such plants, such as the fruits, blossoms, leaves, stems, tubers or roots, while in some cases plant parts that grow later are still protected against those pests.

Target crops include especially cereals, such as wheat, barley, rye, oats, rice, maize and sorghum; beet, such as sugar beet and fodder beet; fruit, e.g. pomes, stone fruit and soft fruit, such as apples, pears, plums, peaches, almonds, cherries and berries, e.g. strawberries, raspberries and blackberries; leguminous plants, such as beans, lentils, peas and soybeans; oil plants, such as rape, mustard, poppy, olives, sunflowers, coconut, castor oil, cocoa and groundnuts; cucurbitaceae, such as marrows, cucumbers and melons; fibre plants, such as cotton, flax, hemp and jute; citrus fruits, such as oranges, lemons, grapefruit and mandarins; vegetables, such as spinach, lettuce, asparagus, cabbages, carrots, onions, tomatoes, potatoes and paprika; lauraceae, such as avocado, cinnamon and camphor; and tobacco, nuts, coffee, aubergines, sugar cane, tea, pepper, vines, hops, bananas, natural rubber plants and ornamentals.

Further areas of use of the compounds according to the invention are the protection of stored goods and storerooms and the protection of raw materials, and also in the hygiene sector, especially the protection of domestic animals and productive livestock against pests of the mentioned type, more especially the protection of domestic animals, especially cats and dogs, from attack by fleas, ticks and nematodes.

The invention therefore relates also to pesticidal compositions, such as emulsifiable concentrates, suspension concentrates, directly sprayable or dilutable solutions, spreadable pastes, dilute emulsions, wettable powders, soluble powders, dispersible powders, wettable powders, dusts, granules and encapsulations of polymer substances, that comprise at least one of the compounds according to the invention, the choice of formulation being made in accordance with the intended objectives and the prevailing circumstances.

The active ingredient is used in those compositions in pure form, a solid active ingredient, for example, in a specific particle size, or preferably together with at least one of the adjuvants customary in formulation technology, such as extenders, e.g. solvents or solid carriers, or surface-active compounds (surfactants). In the area of parasite control in humans, domestic animals, productive livestock and pets it will be self-evident that only physiologically tolerable additives are used.

As formulation adjuvants there are used, for example, solid carriers, solvents, stabilisers, "slow release" adjuvants, colourings and optionally surface-active substances (surfactants). Suitable carriers and adjuvants include all substances customarily used. As adjuvants, such as solvents, solid carriers, surface-active compounds, non-ionic surfactants, cationic surfactants, anionic surfactants and further adjuvants in the compositions used according to the invention, there come into consideration, for example, those described in EP-A-736 252, page 7, line 51 to page 8, line 39.

The compositions for use in crop protection and in humans, domestic animals and productive livestock generally comprise from 0.1 to 99%, especially from 0.1 to 95%, of active ingredient and from 1 to 99.9%, especially from 5 to 99.9%, of at least one solid or liquid adjuvant, the composition generally including from 0 to 25%, especially from 0.1 to 20%, of surfactants (%=% by weight in each case). Whereas commercial products will preferably be formulated as concentrates, the end user will normally employ dilute formulations having considerably lower concentrations of active ingredient.

Preferred crop protection products have especially the following compositions (%=percent by weight):

| Emulsifiable concentrates: | |
|---|---|
| active ingredient: | 1 to 90%, preferably 5 to 20% |
| surfactant: | 1 to 30%, preferably 10 to 20% |
| solvent: | 5 to 98%, preferably 70 to 85% |

-continued

| Dusts: | |
|---|---|
| active ingredient: | 0.1 to 10%, preferably 0.1 to 1% |
| solid carrier: | 99.9 to 90%, preferably 99.9 to 99% |
| Suspension concentrates: | |
| active ingredient: | 5 to 75%, preferably 10 to 50% |
| water: | 94 to 24%, preferably 88 to 30% |
| surfactant: | 1 to 40%, preferably 2 to 30% |
| Wettable powders: | |
| active ingredient: | 0.5 to 90%, preferably 1 to 80% |
| surfactant: | 0.5 to 20%, preferably 1 to 15% |
| solid carrier: | 5 to 99%, preferably 15 to 98% |
| Granules: | |
| active ingredient: | 0.5 to 30%, preferably 3 to 15% |
| solid carrier: | 99.5 to 70%, preferably 97 to 85% |

The compositions according to the invention may also comprise further solid or liquid adjuvants, such as stabilisers, e.g. vegetable oils or epoxidised vegetable oils (e.g. epoxidised coconut oil, rapeseed oil or soybean oil), antifoams, e.g. silicone oil, preservatives, viscosity regulators, binders and/or tackifiers as well as fertilisers or other active ingredients for obtaining special effects, e.g. acaricides, bactericides, fungicides, nematicides, molluscicides or selective herbicides.

The crop protection products according to the invention are prepared in known manner, in the absence of adjuvants, e.g. by grinding, sieving and/or compressing a solid active ingredient or mixture of active ingredients, for example to a certain particle size, and in the presence of at least one adjuvant, for example by intimately mixing and/or grinding the active ingredient or mixture of active ingredients with the adjuvant(s). The invention relates likewise to those processes for the preparation of the compositions according to the invention and to the use of the compounds of formula (I) in the preparation of those compositions.

The invention relates also to the methods of application of the crop protection products, i.e. the methods of controlling pests of the mentioned type, such as spraying, atomising, dusting, coating, dressing, scattering or pouring, which are selected in accordance with the intended objectives and the prevailing circumstances, and to the use of the compositions for controlling pests of the mentioned type. Typical rates of concentration are from 0.1 to 1000 ppm, preferably from 0.1 to 500 ppm, of active ingredient. The rates of application per hectare are generally from 1 to 2000 g of active ingredient per hectare, especially from 10 to 1000 g/ha, preferably from 20 to 600 g/ha.

A preferred method of application in the area of crop protection is application to the foliage of the plants (foliar application), the frequency and the rate of application being dependent upon the risk of infestation by the pest in question. However, the active ingredient can also penetrate the plants through the roots (systemic action) when the locus of the plants is impregnated with a liquid formulation or when the active ingredient is incorporated in solid form into the locus of the plants, for example into the soil, e.g. in granular form (soil application). In the case of paddy rice crops, such granules may be applied in metered amounts to the flooded rice field.

The crop protection products according to the invention are also suitable for protecting plant propagation material, e.g. seed, such as fruits, tubers or grains, or plant cuttings, against animal pests. The propagation material can be treated with the composition before planting: seed, for example, can be dressed before being sown. The active ingredients according to the invention can also be applied to grains (coating), either by impregnating the seeds in a liquid formulation or by coating them with a solid formulation. The composition can also be applied to the planting site when the propagation material is being planted, for example to the seed furrow during sowing. The invention relates also to such methods of treating plant propagation material and to the plant propagation material so treated.

PREPARATION EXAMPLES

Preparation of the free bases

Example P1.1

4"-Desoxy-4"-epi-(N-3-fluorophenylmethyl-amino)-avermectin B1

1.0 g of 4"-desoxy-4"-epi-amino-avermectin B1 is dissolved in 12 ml of tetrahydrofuran. 1.8 ml of acetic acid, 0.2 ml of water and 0.18 ml of 3-fluorobenzaldehyde are added. 90 mg of sodium cyanoborohydride are then added. The mixture is stirred at room temperature for 12 hours. Extraction is then carried out with ethyl acetate and saturated sodium chloride solution; the organic phase is dried over sodium sulfate and the solvents are distilled off. The residue is purified by chromatography on silica gel (hexane/ethyl acetate), yielding 4"-desoxy-4"-epi-(N-3-fluorophenylmethyl-amino)-avermectin B1.

Example P1.2

4"-Desoxy-4"-epi-N-ethylamino-avermectin B1

4.0 g of 4"-desoxy-4"-epi-amino-avermectin B1 are dissolved in 24 ml of ethyl acetate. 7.4 ml of ethyl iodide and 24 ml of sodium bicarbonate (1N in water) are added. The mixture is stirred vigorously at room temperature for 14 hours. The phases are then separated; the organic phase is dried over sodium sulfate and the solvents are distilled off. The residue is purified by chromatography on silica gel (hexane/ethyl acetate), yielding 4"-desoxy-4"-epi-N-ethylamino-avermectin B1.

Example P1.3

4"-Desoxy-4"-epi-N-(isopropoxycarbonyl-methyl)-amino-avermectin B1

300 mg of 4"-desoxy-4"-epi-amino-avermectin B1 are dissolved in 3 ml of ethyl acetate. 620 mg of isopropyl bromoacetate and 3 ml of sodium bicarbonate (1N in water) are added. The mixture is stirred vigorously at room temperature for 18 hours. The phases are then separated; the organic phase is dried over sodium sulfate and the solvent is distilled off. The residue is purified by chromatography on silica gel (hexane/ethyl acetate), yielding 4"-desoxy-4"-epi-N-(isopropoxycarbonyl-methyl)-amino-avermectin B1.

Example P2.1

4"-Desoxy-4"-epi-(N-methyl-N-1-propen-3-yl-amino)-avermectin B1

600 mg of 4"-desoxy-4"-epi-methylamino-avermectin B1 are dissolved in 6 ml of ethyl acetate. 0.56 ml of allyl bromide and 6 ml of sodium bicarbonate (1N in water) are added. The mixture is stirred vigorously at 60° C. for 18 hours, then cooled. The phases are then separated; the organic phase is dried over sodium sulfate and the solvent is distilled off. The residue is purified by chromatography on silica gel (hexane/ ethyl acetate), yielding 4"-desoxy-4"-epi-(N-methyl-N-1-propen-3-yl-amino)-avermectin B1.

Example P2.2

4"-Desoxy-4"-epi-(N-2-hydroxyethyl-N-methylamino)-avermectin B1

Step 1: 4.55 g of 4"-desoxy-4"-epi-methylamino-avermectin B1 are dissolved in 45 ml of ethyl acetate. 8.6 g of ethyl bromoacetate and 45 ml of sodium bicarbonate (1N in water) are added. The mixture is stirred vigorously at 60° C. for 18 hours, then cooled. The phases are then separated; the organic phase is dried over sodium sulfate and the solvent is distilled off. The residue is purified by chromatography on silica gel (hexane/ethyl acetate), yielding 4"-desoxy-4"-epi-(N-methyl-N-ethoxycarbonylmethyl-amino)-avermectin B1.

Step 2: 300 mg of 4"-desoxy-4"-epi-(N-methyl-N-ethoxycarbonylmethyl-amino)-avermectin B1 are dissolved in 6 ml of toluene. With stirring at room temperature, 1.3 ml of diisobutylaluminium hydride (1.2 mol/l in toluene) are added. After 15 minutes, extraction is carried out with ethyl acetate and saturated ammonium chloride solution. The phases are then separated; the organic phase is dried over sodium sulfate and the solvent is distilled off. The residue is purified by chromatography on silica gel (ethyl acetate/methanol), yielding 4"-desoxy-4"-epi-(N-2-hydroxyethyl-N-methylamino)-avermectin B1.

Example P2.3

4"-Desoxy-4"-epi-(N-isopropyl-N-methylamino)-avermectin B1

2.0 g of 4"-desoxy-4"-epi-isopropylamino-avermectin B1 are dissolved in 20 ml of ethyl acetate. 4 ml of methyl iodide and 20 ml of sodium bicarbonate (1N in water) are added and the mixture is stirred vigorously at 60° C. for 14 hours, then cooled. The phases are then separated; the organic phase is dried over sodium sulfate and the solvent is distilled off. The residue is purified by chromatography on silica gel (ethyl acetate), yielding 4"-desoxy-4"-epi-(N-isopropyl-N-methylamino)-avermectin B1.

Example P2.4

4"-Desoxy-4"-epi-(N-isopropyl-N-methylamino)-avermectin B1

9.14 g of 4"-desoxy-4"-epi-isopropylamino-avermectin B1 are dissolved in 100 ml of methanol. 15 ml of pivalic acid and 25 ml of formaldehyde solution (37% in water) are added. 0.7 g of sodium cyanoborohydride is then added. The mixture is stirred at room temperature for 1 hour, then the methanol is evaporated off in vacuo and the residue is extracted with ethyl acetate and saturated sodium bicarbonate solution. The phases are then separated; the organic phase is dried over sodium sulfate and the solvent is distilled off. The residue is purified by chromatography on silica gel (ethyl acetate/methanol), yielding 4"-desoxy-4"-epi-(N-isopropyl-N-methylamino)-avermectin B1.

Example P2.5

4"-Desoxy-4"-epi-(N-carboxymethyl-N-methylamino)-avermectin B1

Step 1: 10 g of 4"-desoxy-4"-epi-methylamino-avermectin B1 are dissolved in 100 ml of ethyl acetate. 15.6 g of benzyl bromoacetate and 100 ml of sodium bicarbonate (1N in water) are added. The mixture is stirred vigorously at 60° C. for 5 days, then cooled. The phases are then separated; the organic phase is dried over sodium sulfate and the solvent is distilled off. The residue is purified by chromatography on silica gel (hexane/ethyl acetate), yielding 4"-desoxy-4"-epi-(N-benzyloxycarbonyl-methyl-N-methylamino)-avermectin B1.

Step 2: 7.8 g of 4"-desoxy-4"-epi-(N-benzyloxycarbonyl-methyl-N-methylamino)-avermectin B1 are dissolved in 100 ml of tetrahydrofuran. 780 mg of palladium (5% on carbon) are added and hydrogenation is carried out at normal pressure and room temperature. After one hour the absorption of hydrogen has ceased. The mixture is filtered over Celite and the solvent is evaporated off, yielding 4"-desoxy-4"-epi-(N-carboxymethyl-N-methylamino)-avermectin B1.

Example P2.6

4"-Desoxy-4"-epi-(N-carboxymethyl-N-methylamino)-avermectin B1

Step 1: 15 g of 4"-desoxy-4"-epi-methylamino-avermectin B1 are dissolved in 120 ml of ethyl acetate. 26 g of methyl bromoacetate and 120 ml of sodium bicarbonate (1N in water) are added. The mixture is stirred vigorously at 60° C. for 5 days, then cooled. The phases are then separated; the organic phase is dried over sodium sulfate and the solvent is distilled off. The residue is purified by chromatography on silica gel (hexane/ethyl acetate), yielding 4"-desoxy-4"-epi-(N-methoxycarbonyl-methyl-amino-N-methyl)-avermectin B1.

Step 2: 10 g of 4"-desoxy-4"-epi-(N-methoxycarbonylm-ethyl-amino-N-methyl)-avermectin B1 are dissolved in 90 ml of tetrahydrofuran. 10 ml of water and 440 mg of lithium hydroxide monohydrate are added and stirring is carried out at room temperature for 14 hours. Extraction is then carried out with water and diethyl ether, and the aqueous phase is separated off and lyophilised. The residue is extracted with ethyl acetate and citric acid (10% in water); the organic phase is dried over sodium sulfate and the solvent is distilled off, yielding 4"-desoxy-4"-epi-(N-carboxymethyl-N-methylamino)-avermectin B1.

Example P2.7

4'-Desoxy-4"-epi-(N-ethyl-N-methylamino)-avermectin B1

8.0 g of 4"-desoxy-4"-epi-N-methylamino-avermectin B1 are dissolved in 50 ml of ethyl acetate. 15 ml of ethyl iodide and 50 ml of sodium bicarbonate (1N in water) are added. The mixture is stirred vigorously at 60° C. for 2 days. The phases are then separated; the organic phase is dried over sodium sulfate and the solvents are distilled off. The residue is purified by chromatography on silica gel (ethyl acetate/methanol), yielding 4"-desoxy-4"-epi-(N-ethyl-N-methylamino)-avermectin B1.

Example P2.8

4"-Desoxy-4"-epi-{N-[(1-benzyloxycarbonyl-ethyl-carbamoyl)-methyl]-N-methylamino}-avermectin B1

500 mg of 4"-desoxy-4"-epi-(N-carboxymethyl-N-methylamino)-avermectin B are dissolved in 5 ml of ethyl acetate, then 170 mg of L-alanine benzyl ester, 72 mg of 1-hydroxy-7-aza-benzotriazole and 110 mg of N,N-dicyclohexylcarbodiimide are added. Stirring is carried out at room temperature for 7 days. The mixture is then extracted with ethyl acetate and sodium bicarbonate (1N in water); the organic phase is dried over sodium sulfate and the solvent is distilled off. The residue is purified by chromatography on silica gel (hexane/ethyl acetate), yielding 4"-desoxy-4"-epi-{N-[(1-benzyloxycarbonyl-ethylcarbamoyl)-methyl]-N-methylamino}-avermectin B1.

Example P2.9

4"-Desoxy-4"-epi-{N-[(1-carboxy-ethylcarbamoyl)-methyl]-N-methyl-amino}-avermectin B1

160 mg of 4"-desoxy-4"-epi-{N-[(1-benzyloxycarbonyl-ethylcarbamoyl)-methyl]-N-methylamino}-avermectin B1 are dissolved in 10 ml of tetrahydrofuran. 50 mg of palladium (5% on carbon) are added and hydrogenation is carried out at normal pressure and room temperature. After 3 hours the absorption of hydrogen has ceased. The mixture is filtered over Celite and the solvent is evaporated off, yielding 4"-desoxy-4"-epi-{N-[(1-carboxy-ethyl-carbamoyl)-methyl]-N-methylamino}-avermectin B1.

Example P2.10

4"-Desoxy-4"-epi-[N-(2-hydroxy-2-methyl-propyl)-N-methylamino]-avermectin B1

300 mg of 4"-desoxy-4"-epi-(N-methyl-N-ethoxycarbonylmethyl-amino)-avermectin B1 (Step 1 from P2.2) are dissolved in 6 ml of tetrahydrofuran. With stirring at room temperature, 0.64 ml of methylmagnesium bromide (3 mol/l in diethyl ether) is added. After one hour, extraction is carried out with ethyl acetate and saturated ammonium chloride solution. The phases are then separated; the organic phase is dried over sodium sulfate and the solvents are distilled off. The residue is purified by chromatography on silica gel (ethyl acetate/methanol), yielding 4"-desoxy-4"-epi-[N-(2-hydroxy-2-methyl-propyl)-N-methyl-amino]-avermectin B1.

Example P3.1

4"-Desoxy-4"-epi-[N,N-bis(1-phenyl-1-propen-3-yl)amino]-avermectin B1

3.48 g of 4"-desoxy-4"-epi-amino-avermectin B1 are dissolved in 40 ml of ethyl acetate. 4.62 g of 3-bromo-1-phenyl-1-propene and 40 ml of sodium bicarbonate (1N in water) are added. The mixture is stirred vigorously at 60° C. for 3 days and then cooled. The phases are then separated; the organic phase is dried over sodium sulfate and the solvent is distilled off. The residue is purified by chromatography on silica gel (hexane/ethyl acetate) yielding 4"-desoxy-4"-epi-[N,N-bis(1-phenyl-1-propen-3-yl)amino]-avermectin B1.

Example P3.2

4"-Desoxy-4"-epi-(azetidin-1-yl)-avermectin B1

300 mg of 4"-desoxy-4"-epi-amino-avermectin B1 are dissolved in 1 ml of toluene. 0.106 ml of 1,3-dibromopropane and 1 ml of sodium bicarbonate (1N in water) are added. The mixture is stirred vigorously at 90° C. for 24 hours, then cooled. The phases are then separated; the organic phase is dried over sodium sulfate and the solvent is distilled off. The residue is purified by chromatography on silica gel (ethyl acetate/methanol), yielding 4"-desoxy-4"-epi-(azetidin-1-yl)-avermectin B1.

Example P3.3

4"-Desoxy-4"-epi-[N,N-bis(3,3-dimethyl-butyl)amino]-avermectin B1

0.87 g of 4"-desoxy-4"-epi-amino-avermectin B1 is dissolved in 10 ml of tetrahydrofuran. 1 ml of pivalic acid, 0.1 ml of water and 0.60 g of 3,3-dimethylbutyraldehyde are added. 0.38 g of sodium cyanoborohydride is then added. The mixture is stirred at room temperature for 14 hours. Extraction is then carried out with ethyl acetate and sodium bicarbonate (1N in water); the organic phase is dried over sodium sulfate and the solvents are distilled off. The residue is purified by chromatography on silica gel (hexane/ethyl acetate), yielding 4"-desoxy-4"-epi-[N,N-bis(3,3-dimethyl-butyl)amino]-avermectin B1.

Preparation of Salts of Formula (I)

Example P4.1

Preparation of 4"-deoxy-4"-epi-N,N-dimethylammonium-avermectin B1 benzoate 500 mg of 4"-desoxy-4"-epi-N,N-dimethylamino-avermectin B1 and 67 mg of benzoic acid are dissolved in 5 ml of dichloromethane. The solvent is evaporated off and the residue is suspended in diethyl ether and filtered off over a glass frit. The filtration residue is washed with diethyl ether and dried on the frit in a stream of air. 4"-Deoxy-4"-epi-N,N-dimethyl-ammonium-avermectin B1 benzoate is obtained.

Example P4.2

Preparation of 4"-deoxy-4"-epi-N,N-dimethylammonium-avermectin B1 maleate (1:1)

500 mg of 4"-desoxy-4"-epi-N,N-dimethylamino-avermectin B1 and 64 mg of maleic acid are dissolved in 5 ml of dichloromethane. The solvent is evaporated off and the residue is suspended in diethyl ether and filtered off over a glass frit. The filtration residue is washed with diethyl ether and dried on the frit in a stream of air. 4"-Deoxy-4"-epi-N,N-dimethyl-ammonium-avermectin B1 maleate is obtained.

Example P4.3

Preparation of 4"-deoxy-4"-epi-N,N-dimethylammonium-avermectin B1 salicylate 500 mg of 4"-desoxy-4"-epi-N,N-dimethylamino-avermectin B1 and 76 mg of salicylic acid are dissolved in 5 ml of dichloromethane. The solvent is evaporated off and the residue is suspended in diethyl ether and filtered off over a glass frit. The filtration residue is washed with diethyl ether and dried on the frit in a stream of air. 4"-Deoxy-4"-epi-N,N-dimethyl -ammonium-avermectin B1 salicylate is obtained.

Example P4.4

Preparation of 4"-deoxy-4"-epi-N,N-dimethylammonium-avermectin B1 citrate (1:1)

500 mg of 4"-deoxy-4"-epi-N,N-dimethylamino-avermectin B1 and 106 mg of citric acid are dissolved in 5 ml of dichloromethane. The solvent is evaporated off and the residue is suspended in diethyl ether and filtered off over a glass frit. The filtration residue is washed with diethyl ether and dried on the frit in a stream of air. 4"-Deoxy-4"-epi-N,N-dimethyl -ammonium-avermectin B1 citrate is obtained.

Example P4.5

Preparation of 4"-deoxy-4"-epi-N,N-dimethylammonium-avermectin B1 benzenesulfonate 500 mg of 4"-deoxy-4"-epi-N,N-dimethylamino-avermectin B1 and 87 mg of benzene -sulfonic acid are dissolved in 5 ml of acetonitrile. The solvent is evaporated off and the residue is suspended in diethyl ether and filtered off over a glass frit. The filtration residue is washed with diethyl ether and dried on the frit in a stream of air. 4"-Deoxy-4"-epi-N,N -dimethylammonium-avermectin B1 benzenesulfonate is obtained.

Example P5.1

Preparation of 4"-deoxy-4"-epi-N-isopropylammonium-avermectin B1 benzoate 300 mg of 4"-deoxy-4"-epi-N-isopropylamino-avermectin B1 and 38 mg of benzoic acid are dissolved in 1 ml of acetonitrile. The solvent is evaporated off and the residue is suspended in a small amount of hexane and filtered off over a glass frit. The filtration residue is dried on the frit in a stream of air. 4"-Deoxy-4"-epi-N-isopropylammonium -avermectin B1 benzoate is obtained.

Example P5.2

Preparation of 4"-deoxy-4"-epi-N-isopropylammonium-avermectin B1 maleate (1:1)

300 mg of 4"-deoxy-4"-epi-N-isopropylamino-avermectin B1 and 36 mg of maleic acid are dissolved in 1 ml of aceto nitrile. 3 ml of toluene are added and then 20 ml of hexane. The mixture is filtered over a glass frit, washed with hexane and dried on the frit in a stream of air. 4"-Deoxy-4"-epi-N-isopropylammonium-avermectin B1 maleate is obtained.

Example P5.3

Preparation of 4"-deoxy-4"-epi-N-isopropylammonium-avermectin B1 salicylate 300 mg of 4"-deoxy-4"-epi-N-isopropylamino-avermectin B1 and 43 mg of salicylic acid are dissolved in 1 ml of acetonitrile. 3 ml of toluene are added and then 20 ml of hexane. The mixture is filtered over a glass frit, washed with hexane and dried on the frit in a stream of air. 4"-Deoxy-4"-epi-N-isopropylammonium-avermectin B1 salicylate is obtained.

Example P5.4

Preparation of 4"-deoxy-4"-epi-N-isopropylammonium-avermectin B1 citrate (1:1)

300 mg of 4"-deoxy-4"-epi-N-isopropylamino-avermectin B1 and 65 mg of citric acid are dissolved in 1 ml of acetonitrile. 3 ml of toluene are added and then 20 ml of hexane. The mixture is filtered over a glass frit, washed with hexane and dried on the frit in a stream of air. 4"-Deoxy-4"-epi-N-isopropylammonium-avermectin B1 citrate is obtained.

Example P5.5

Preparation of 4"-deoxy-4"-epi-N-isopropylammonium-avermectin B1 benzenesulfonate 300 mg of 4"-deoxy-4"-epi-N-isopropylamino-avermectin B1 and 49 mg of benzene -sulfonic acid are dissolved in 1 ml of acetonitrile. 3 ml of toluene are added and then 20 ml of hexane. The mixture is filtered over a glass frit, washed with hexane and dried on the frit in a stream of air. 4'-Deoxy-4"-epi-N-isopropylammonium-avermectin B1 citrate is obtained.

Example P6.1

Analogously to the above Preparation Examples it is also possible to prepare the compounds listed in Tables 1 to 60.

TABLE A

Compounds of formula (I) can be formed especially with the following acids:

| No. | | |
|---|---|---|
| A.1) | 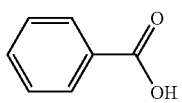 | benzoic acid |
| A.2) | cis-HOOC—CH=CHCOOH | maleic acid |
| A.3) | trans-HOOC—CH=CHCOOH | fumaric acid |

TABLE A-continued

Compounds of formula (I) can be formed especially with the following acids:

| No. | | |
|---|---|---|
| A.4) | (2-hydroxybenzoic acid structure) | 2-hydroxybenzoic acid, salicyclic acid |
| A.5) | HOOC—CH(OH)CH₂COOH | malic acid |
| A.6) | (benzenesulfonic acid structure, Ph-SO₃H) | benzenesulfonic acid |
| A.7) | (barbituric acid structure) | barbituric acid |
| A.8) | (2-ethylbutyric acid structure) | 2-ethylbutyric acid |
| A.9) | HOOC—CH(SH)CH₂COOH | thiomalic acid |
| A.10) | (3,5-dihydroxy-benzoic acid structure) | 3,5-dihydroxy-benzoic acid |
| A.11) | (trimesic acid structure) | trimesic acid |
| A.12) | (D-(−)-quinic acid structure) | D-(−)-quinic acid |
| A.13) | (2-bromo-benzoic acid structure) | 2-bromo-benzoic acid |

TABLE A-continued

Compounds of formula (I) can be formed especially with the following acids:

| No. | | |
|---|---|---|
| A.14) | [structure] | 2-phenyl-benzoic acid |
| A.15) | [structure] | 3,3'-thiodipropionic acid |
| A.16) | [structure] | naphthalene-1-carboxylic acid |
| A.17) | [structure] | 5-sulfosalicyclic acid |
| A.18) | [structure] | 2-methoxy-phenylacetic acid |
| A.19) | [structure] | benzene-1,2,4-tricarboxylic acid |
| A.20) | [structure] | 3-hydroxy-benzoic acid |
| A.21) | [structure] | D-gluconic acid |

TABLE A-continued

Compounds of formula (I) can be formed especially with the following acids:

| No. | | |
|---|---|---|
| A.22) | 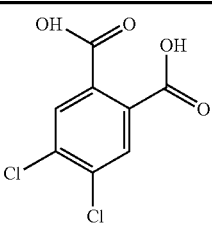 | 4,5-dichloro-phthalic acid |
| A.23) | HOOC—(CH$_2$)$_5$CH$_3$ | n-hexanoic acid (caproic acid) |
| A.24) | HOOC—(CH$_2$)$_7$CH$_3$ | n-heptanoic acid (oenanthic acid) |
| A.25) | HOOC—(CH$_2$)$_8$CH$_3$ | n-octanoic acid (caprylic acid) |
| A.26) | HOOC—(CH$_2$)$_{16}$CH$_3$ | stearic acid |
| A.27) | HOOC—(CH$_2$)$_{14}$CH$_3$ | palmitic acid |
| A.28) | 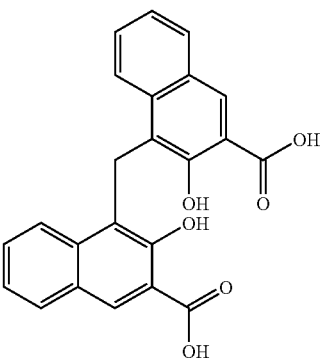 | 2,2'-dihydroxy-1,1'-dinaphthylmethane-3,3'-4,4'-methylene-bis(3-hydroxy-2-naphthoic acid) embonic acid |
| A.29) | 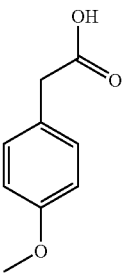 | 4-methoxy-phenylacetic acid homoanisic acid |
| A.30) | 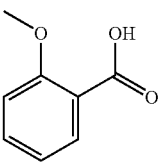 | 2-anisic acid (2-methoxy-benzoic acid) |
| A.31) | 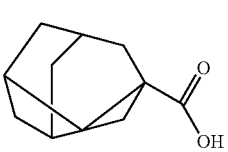 | adamantane-1-carboxylic acid |
| A.32) | 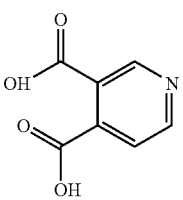 | pyridine-3,4-dicarboxylic acid |

TABLE A-continued

Compounds of formula (I) can be formed especially with the following acids:

| No. | | |
|---|---|---|
| A.33) | 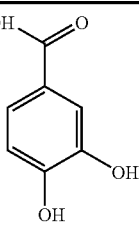 | 3,4-dihydroxy-benzoic acid |
| A.34) | 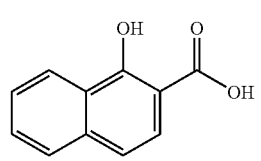 | 1-hydroxy-2-naphthanoic acid<br>(1-naphthol-2-carboxylic acid) |
| A.35) | 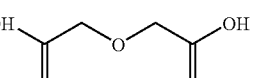 | 2,2'-oxydiacetic acid<br>(diglycolic acid) |
| A.36) | 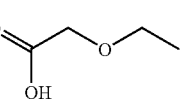 | O-ethyl-glycolic acid |
| A.37) | 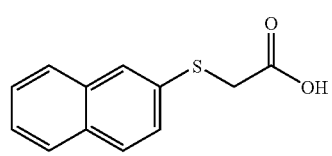 | (2-naphthylthio)-acetic acid<br>(S-(2-naphthyl)-thioglycolic acid) |
| A.38) | 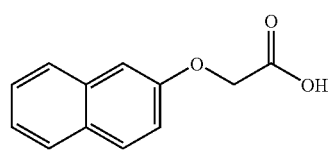 | 2-naphthoxxy-acetic acid |
| A.39) | 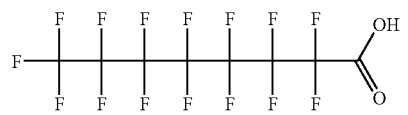 | perfluoro-octanoic acid |
| A.40) | 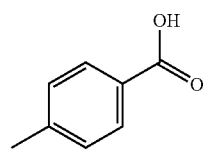 | p-toluic acid |
| A.41) | 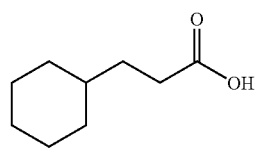 | cyclohexanepropionic acid |
| A.42) | 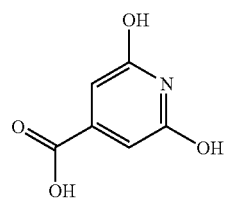 | 2,6-dihydroxypyridine-4-carboxylic acid<br>(citrazinic acid) |

TABLE A-continued

Compounds of formula (I) can be formed especially with the following acids:

| No. | | |
|---|---|---|
| A.43) | [structure] | 3-methoxypropionic acid |
| A.44) | [structure] | 3,4,5-trihydroxy-benzoic acid (gallic acid) |
| A.45) | [structure] | pyromucic acid (furan-2-carboxylic acid) |
| A.46) | [structure] | 2-methyl-benzoic acid (o-toluic acid) |
| A.47) | [structure] | 3,6,9-trioxa-undecanedioic acid |
| A.48) | [structure] | 3-(4-methoxyphenyl)-propionic acid (p-methoxy-hydrocinnamic acid) |
| A.49) | | 3-(3,4-dihydroxyphenyl)-propionic acid |
| A.50) | [structure] | O-acetyl-salicyclic acid (aspirin) |
| A.51) | [structure] | 3-fluoro-benzoic acid |
| A.52) | [structure] | cyclohexanecarboxylic acid |

TABLE A-continued

Compounds of formula (I) can be formed especially with the following acids:

No.

| A.53) | 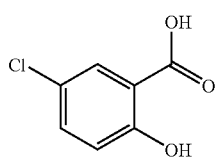 | 5-chloro-2-hydroxy-benzoic acid (5-chloro-salicyclic acid) |
| A.54) | 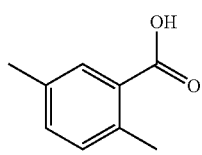 | 2,5-dimethyl-benzoic acid (p-xylic acid) |
| A.55) | 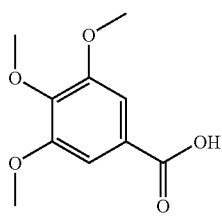 | 3,4,5-trimethoxy-benzoic acid (trimethylgallic acid) |
| A.56) | 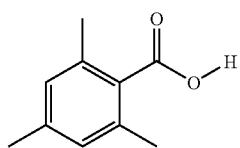 | 2,4,6-trimethyl-benzoic acid |
| A.57) | 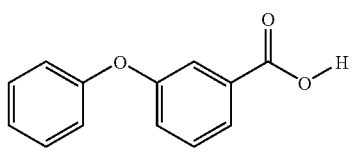 | 3-phenoxy-benzoic acid |
| A.58) | 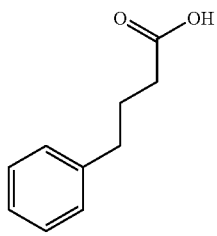 | 4-phenyl-butyric acid |
| A.59) | 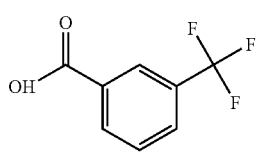 | 3-trifluoromethyl-benzoic acid |
| A.60) | 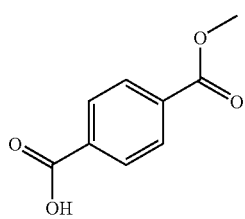 | terephthalic acid monomethyl ester |

TABLE A-continued
Compounds of formula (I) can be formed especially with the following acids:
| No. | | |
|---|---|---|
| A.61) | 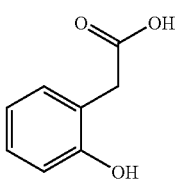 | o-hydroxy-phenylacetic acid |
| A.62) | 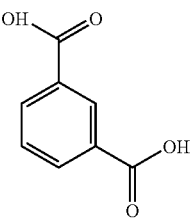 | isophthalic acid |
| A.63) | 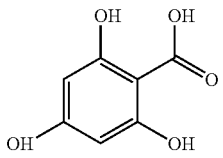 | 2,4,6-trihydroxy-benzoic acid |
| A.64) | 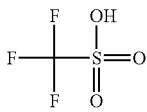 | trifluoromethanesulfonic acid |
| A.65) | 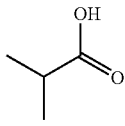 | 2-methyl-propionic acid (isobutyric acid) |
| A.66) | 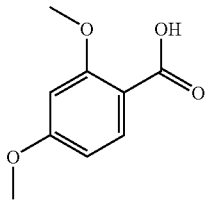 | 2,4-dimethoxy-benzoic acid |
| A.67) | 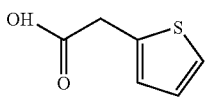 | 2-thienylacetic acid (thiophene-2-acetic acid) |
| A.68) | 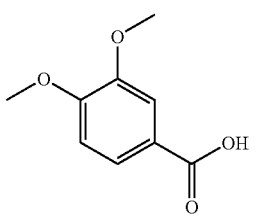 | 3,4-dimethoxy-benzoic acid (veratric acid) |

TABLE A-continued

*Compounds of formula (I) can be formed especially with the following acids:*

| No. | | |
|---|---|---|
| A.69) | 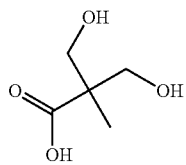 | 2,2-bis(hydroxymethyl)-propionic acid |
| A.70) | 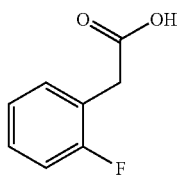 | 2-fluoro-phenylacetic acid |
| A.71) | 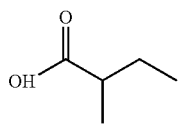 | 2-methyl-butyric acid |
| A.72) | 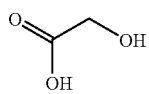 | hydroxy-acetic acid |
| A.73) | 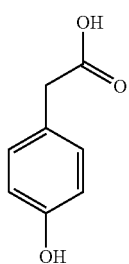 | 4-chloro-phenylacetic acid |
| A.74) | 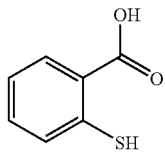 | 2-mercaptobenzoic acid (thiosalicylic acid) |
| A.75) | 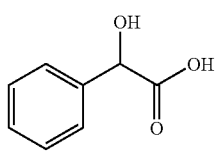 | (+/−)-2-hydroxyphenyl-acetic acid (DL-mandelic acid) |
| A.76) | 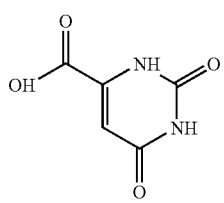 | 2,4-dihydroxypyrimidine-6-carboxylic acid |

TABLE A-continued

Compounds of formula (I) can be formed especially with the following acids:

| No. | | |
|---|---|---|
| A.77) | 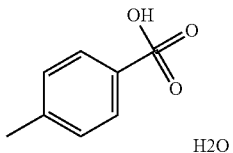 H2O | toluene-4-sulfonic acid (p-toluene-sulfonic acid) |
| A.78) | 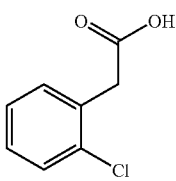 | 2-chloro-phenylacetic acid |
| A.79) | 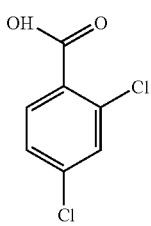 | 2,4-dichloro-benzoic acid |
| A.80) | | 2,6-dichloro-benzoic acid |
| A.81) | 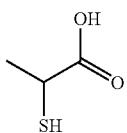 | 2-mercapto-propionic acid (thiolactic acid) |
| A.82) | 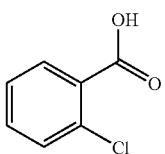 | 2-chloro-benzoic acid |
| A.83) | 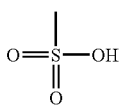 | methanesulfonic acid |
| A.84) | 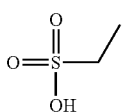 | ethanesulfonic acid (ethyl-sulfuric acid) |
| A.85) | 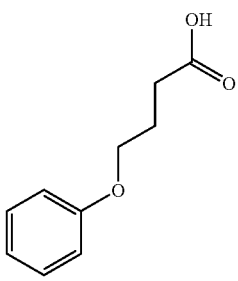 | 4-phenoxy-butyric acid |

TABLE A-continued

Compounds of formula (I) can be formed especially with the following acids:

| No. | | |
|---|---|---|
| A.86) | | 4-tert-butyl-benzoic acid |
| A.87) | | 3,4-methylenedioxy-benzoic acid |
| A.88) | | bis(2-carboxyethyl) disulfide |
| A.89) | | pivalic acid<br>(trimethylacetic acid) |
| A.90) | | nicotinic acid N-oxide |
| A.91) | | acrylic acid |
| A.92) | | 3-benzoylpropionic acid<br>(4-oxo-4-phenyl-butyric acid) |
| A.93) | | (1R)-(−)-camphor-10-sulfonic acid hydrate |

TABLE A-continued
Compounds of formula (I) can be formed especially with the following acids:
| No. | | |
|---|---|---|
| A.94) | 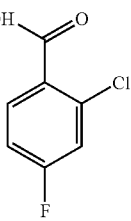 | 2-chloro-4-fluoro-benzoic acid |
| A.95) | 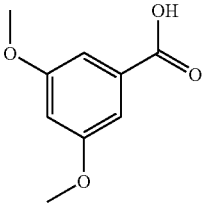 | 3,5-dimethoxy-benzoic acid |
| A.96) | 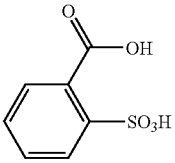 | 2-sulfobenzoic acid |
| A.97) | 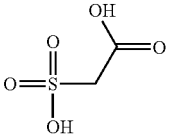 | sulfoacetic acid |
| A.98) | 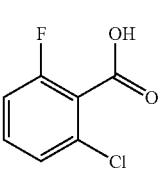 | 2-chloro-6-fluoro-benzoic acid |
| A.99) | 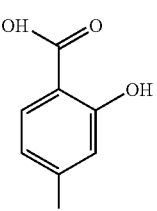 | 2,4-dihydroxy-benzoic acid |
| A.100) | 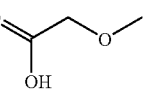 | methoxyacetic acid |
| A.101) | 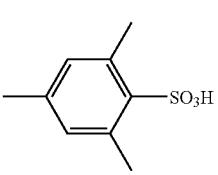 | 2,4,6-trimethyl-benzenesulfonic acid |

TABLE A-continued

Compounds of formula (I) can be formed especially with the following acids:

| No. | | |
|---|---|---|
| A.102) | 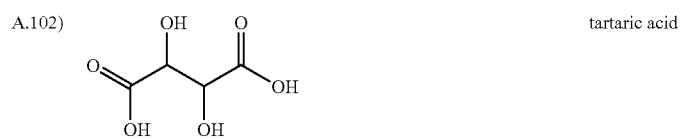 | tartaric acid |
| A.103) |  | xanthene-9-carboxylic acid |
| A.104) |  | 4-pentenoic acid<br>(allylacetic acid) |
| A.105) |  | 5-sulfosalicyclic acid |
| A.106) |  | vinylacetic acid |
| A.107) |  | 2-butynedioic acid<br>(acetylenedicarboxylic acid) |
| A.108) |  | 2-oxo-propionic acid<br>(pyruvic acid) |
| A.109) |  | cyclohexylacetic acid |
| A.110) |  | 2-hydroxyisobutyric acid |

TABLE A-continued

Compounds of formula (I) can be formed especially with the following acids:

No.

A.111) 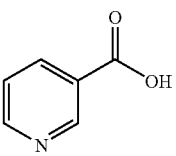 nicotinic acid

A.112) 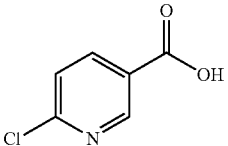 6-chloro-nicotinic acid

A.113) 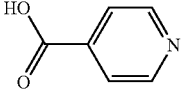 isonicotinic acid

A.114) 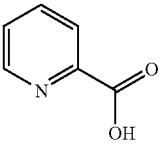 picolinic acid

A.115) 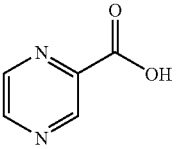 pyrazinecarboxylic acid

| A.116) | HOOC—COOH | oxalic acid |
|---|---|---|
| A.117) | $CH_3CH_2COOH$ | propionic acid |
| A.118) | $CF_3CF_2COOH$ | pentafluoropropionic acid |
| A.119) | $CH_3(CH_2)_2COOH$ | butyric acid |
| A.120) | $CF_3CF_2CF_2COOH$ | heptafluorobutyric acid |
| A.121) | $CH_3(CH_2)_3COOH$ | valeric acid |

A.122) 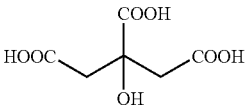 citric acid

| A.123) | $HOCH_2CH(OH)COOH$ | glyceric acid |
|---|---|---|
| A.124) | $CH_3COOH$ | acetic acid |
| A.125) | $ClCH_2COOH$ | chloroacetic acid |
| A.126) | $Cl_2CHCOOH$ | dichloroacetic acid |
| A.127) | $CF_3COOH$ | trifluoroacetic acid |
| A.128) | $FCH_2COOH$ | fluoroacetic acid |
| A.129) | $CH_3CH(OH)COOH$ | lactic acid |
| A.130) | $HOOCCH_2COOH$ | malonic acid |
| A.131) | $HOOC—(CH_2)_2COOH$ | succinic acid |
| A.132) | $HOOC—(CH_2)_3COOH$ | glutaric acid |
| A.133) | $HOOC—(CH_2)_4COOH$ | adipic acid |
| A.134) | $HOOC—(CH_2)_5COOH$ | pimelic acid |
| A.135) | $HOOC—(CH_2)_6COOH$ | suberic acid |
| A.136) | $HOOC—(CH_2)_7COOH$ | azelaic acid |
| A.137) | $HOOC—(CH_2)_8COOH$ | sebacic acid |

A.138) 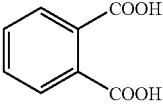 phthalic acid

TABLE A-continued

Compounds of formula (I) can be formed especially with the following acids:

| No. | | |
|---|---|---|
| A.139) | HOOC—⟨benzene⟩—COOH | terephthalic acid |
| A.140) | $H_3PO_4$ | phosphoric acid |
| A.141) | $H_2SO_4$ | sulfuric acid |
| A.142) | HCl | hydrochloric acid |
| A.143) | HBr | hydrobromic acid |
| A.144) | HI | hydriodic acid |
| A.145) | $HNO_3$ | nitric acid |
| A.146) | $HClO_4$ | perchloric acid |
| A.147) | $CH_3C(\!=\!O)\!-\!CH_2\!-\!COOH$ | acetoacetic acid |
| A.148) | $NC\!-\!CH_2\!-\!COOH$ | cyanoacetic acid |
| A.149) | ⟨furan⟩—COOH | tetrahydrofuran-2-carboxylic acid |
| A.150) | CH≡C—COOH | propionic acid |
| A.151) | $H_2C\!=\!C(CH_3)\!-\!COOH$ | methacrylic acid |
| A.152) | $CH_3\!-\!CH\!=\!CH\!-\!COOH$ | crotonic acid |
| A.153) | 2,4,6-trinitrophenol structure | picric acid |

Table 1: A compound of formula (I) wherein $R_1$ is isopropyl and $R_2$ and $R_3$ are hydrogen, and $X^-$ in each case corresponds to the anion of one of the acids mentioned in lines A.1 to A.153 of Table A.

Table 2: A compound of formula (I) wherein $R_1$ is isopropyl, $R_2$ is methyl and $R_3$ is methyl, and $X^-$ in each case corresponds to the anion of one of the acids mentioned in lines A.1 to A.153 of Table A.

Table 3: A compound of formula (I) wherein $R_1$ is isopropyl, $R_2$ is methyl and $R_3$ is ethyl, and $X^-$ in each case corresponds to the anion of one of the acids mentioned in lines A.1 to A.153 of Table A.

Table 4: A compound of formula (I) wherein $R_1$ is isopropyl, $R_2$ is methyl and $R_3$ is n-propyl, and $X^-$ in each case corresponds to the anion of one of the acids mentioned in lines A.1 to A.153 of Table A.

Table 5: A compound of formula (I) wherein $R_1$ is isopropyl, $R_2$ is methyl and $R_3$ is isopropyl, and $X^-$ in each case corresponds to the anion of one of the acids mentioned in lines A.1 to A.153 of Table A.

Table 6: A compound of formula (I) wherein $R_1$ is isopropyl, $R_2$ is methyl and $R_3$ is n-butyl, and $X^-$ in each case corresponds to the anion of one of the acids mentioned in lines A.1 to A.153 of Table A.

Table 7: A compound of formula (I) wherein $R_1$ is isopropyl, $R_2$ is methyl and $R_3$ is isobutyl, and $X^-$ in each case corresponds to the anion of one of the acids mentioned in lines A.1 to A.153 of Table A.

Table 8: A compound of formula (I) wherein $R_1$ is isopropyl, $R_2$ is methyl and $R_3$ is sec-butyl, and $X^-$ in each case corresponds to the anion of one of the acids mentioned in lines A.1 to A.153 of Table A.

Table 9: A compound of formula (I) wherein $R_1$ is isopropyl, $R_2$ is methyl and $R_3$ is tert-butyl, and $X^-$ in each case corresponds to the anion of one of the acids mentioned in lines A.1 to A.153 of Table A.

Table 10: A compound of formula (I) wherein $R_1$ is isopropyl, $R_2$ and $R_3$ are ethyl, and $X^-$ in each case corresponds to the anion of one of the acids mentioned in lines A.1 to A.153 of Table A.

Table 11: A compound of formula (I) wherein $R_1$ is isopropyl, $R_2$ is methyl and $R_3$ is —$CH_2$—CH=$CH_2$, and $X^-$ in each case corresponds to the anion of one of the acids mentioned in lines A.1 to A.153 of Table A.

Table 12: A compound of formula (I) wherein $R_1$ is isopropyl, $R_2$ is methyl and $R_3$ is —$CH_2$—C(=O)$OC_2H_5$, and $X^-$ in each case corresponds to the anion of one of the acids mentioned in lines A.1 to A.153 of Table A.

Table 13: A compound of formula (I) wherein $R_1$ is isopropyl, $R_2$ is methyl and $R_3$ is benzyl, and $X^-$ in each case corresponds to the anion of one of the acids mentioned in lines A.1 to A.153 of Table A.

Table 14: A compound of formula (I) wherein $R_1$ is isopropyl, $R_2$ and $R_3$ together are —$CH_2$—$CH_2$—$CH_2$—, and $X^-$ in each case corresponds to the anion of one of the acids mentioned in lines A.1 to A.153 of Table A.

Table 15: A compound of formula (I) wherein $R_1$ is isopropyl, $R_2$ and $R_3$ together are —$CH_2$—$CH_2$—$CH_2$—$CH_2$—, and $X^-$ in each case corresponds to the anion of one of the acids mentioned in lines A.1 to A.153 of Table A.

Table 16: A compound of formula (I) wherein $R_1$ is isopropyl, $R_2$ is methyl and $R_3$ is —$CH_2$—$CH_2$—OH, and $X^-$ in each case corresponds to the anion of one of the acids mentioned in lines A.1 to A.153 of Table A.

Table 17: A compound of formula (I) wherein $R_1$ is isopropyl, $R_2$ is methyl and $R_3$ is —$CH_2$—$C(CH_3)$OH, and $X^-$ in each case corresponds to the anion of one of the acids mentioned in lines A.1 to A.153 of Table A.

Table 18: A compound of formula (I) wherein $R_1$ is isopropyl, $R_2$ is hydrogen and $R_3$ is ethyl, and $X^-$ in each case corresponds to the anion of one of the acids mentioned in lines A.1 to A.153 of Table A.

Table 19: A compound of formula (I) wherein $R_1$ is isopropyl, $R_2$ is hydrogen and $R_3$ is —$CH_2$—CH=$CH_2$, and $X^-$ in each case corresponds to the anion of one of the acids mentioned in lines A.1 to A.153 of Table A.

Table 20: A compound of formula (I) wherein $R_1$ is isopropyl, $R_2$ is hydrogen and $R_3$ is —$CH_2$—CH≡CH, and $X^-$ in each case corresponds to the anion of one of the acids mentioned in lines A.1 to A.153 of Table A.

Table 21: A compound of formula (I) wherein $R_1$ is isopropyl, $R_2$ is methyl and $R_3$ is —$CH_2$—CH≡CH, and $X^-$ in each case corresponds to the anion of one of the acids mentioned in lines A.1 to A.153 of Table A.

Table 22: A compound of formula (I) wherein $R_1$ is isopropyl, $R_2$ is hydrogen and $R_3$ is isopropyl, and $X^-$ in each case corresponds to the anion of one of the acids mentioned in lines A.1 to A.153 of Table A.

Table 23: A compound of formula (I) wherein $R_1$ is isopropyl, $R_2$ is hydrogen and $R_3$ is n-propyl, and $X^-$ in each case corresponds to the anion of one of the acids mentioned in lines A.1 to A.153 of Table A.

Table 24: A compound of formula (I) wherein $R_1$ is isopropyl, $R_2$ is hydrogen and $R_3$ is n-butyl, and $X^-$ in each case corresponds to the anion of one of the acids mentioned in lines A.1 to A.153 of Table A.

Table 25: A compound of formula (I) wherein $R_1$ is isopropyl, $R_2$ is hydrogen and $R_3$ is —$CH_2$—$CH(CH_3)_2$, and $X^-$ in each case corresponds to the anion of one of the acids mentioned in lines A.1 to A.153 of Table A.

Table 26: A compound of formula (I) wherein $R_1$ is isopropyl, $R_2$ is hydrogen and $R_3$ is

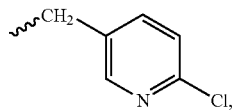

and $X^-$ in each case corresponds to the anion of one of the acids mentioned in lines A.1 to A.153 of Table A.

Table 27: A compound of formula (I) wherein $R_1$ is isopropyl, $R_2$ is hydrogen and $R_3$ is

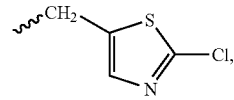

and $X^-$ in each case corresponds to the anion of one of the acids mentioned in lines A.1 to A.153 of Table A.

Table 28: A compound of formula (I) wherein $R_1$ is isopropyl, $R_2$ is hydrogen and $R_3$ is —$CH_2$—C(=O)$OC_2H_5$, and $X^-$ in each case corresponds to the anion of one of the acids mentioned in lines A.1 to A.153 of Table A.

Table 29: A compound of formula (I) wherein $R_1$ is isopropyl, $R_2$ is hydrogen and $R_3$ is —$CH_2$—$C_6H_4$—O—$CF_2$H, and $X^-$ in each case corresponds to the anion of one of the acids mentioned in lines A.1 to A.153 of Table A.

Table 30: A compound of formula (I) wherein $R_1$ is isopropyl, $R_2$ is methyl and $R_3$ is —$CH_2$—CH=CH—C(=O)$OCH_2$C(=O)$C_6H_5$, and $X^-$ in each case corresponds to the anion of one of the acids mentioned in lines A.1 to A.153 of Table A.

Table 31: A compound of formula (I) wherein $R_1$ is sec-butyl and $R_2$ and $R_3$ are hydrogen, and $X^-$ in each case corresponds to the anion of one of the acids mentioned in lines A.1 to A.1 53 of Table A.

Table 32: A compound of formula (I) wherein $R_1$ is sec-butyl, $R_2$ is methyl and $R_3$ is methyl, and $X^-$ in each case corresponds to the anion of one of the acids mentioned in lines A.1 to A.153 of Table A.

Table 33: A compound of formula (I) wherein $R_1$ is sec-butyl, $R_2$ is methyl and $R_3$ is ethyl, and $X^-$ in each case corresponds to the anion of one of the acids mentioned in lines A.1 to A.153 of Table A.

Table 34: A compound of formula (I) wherein $R_1$ is sec-butyl, $R_2$ is methyl and $R_3$ is n-propyl, and $X^-$ in each case corresponds to the anion of one of the acids mentioned in lines A.1 to A.153 of Table A.

Table 35: A compound of formula (I) wherein $R_1$ is sec-butyl, $R_2$ is methyl and $R_3$ is isopropyl, and $X^-$ in each case corresponds to the anion of one of the acids mentioned in lines A.1 to A.153 of Table A.

Table 36: A compound of formula (I) wherein $R_1$ is sec-butyl, $R_2$ is methyl and $R_3$ is n-butyl, and $X^-$ in each case corresponds to the anion of one of the acids mentioned in lines A.1 to A.153 of Table A.

Table 37: A compound of formula (I) wherein $R_1$ is sec-butyl, $R_2$ is methyl and $R_3$ is isobutyl, and $X^-$ in each case corresponds to the anion of one of the acids mentioned in lines A.1 to A.153 of Table A.

Table 38: A compound of formula (I) wherein $R_1$ is sec-butyl, $R_2$ is methyl and $R_3$ is sec-butyl, and $X^-$ in each case corresponds to the anion of one of the acids mentioned in lines A.1 to A.153 of Table A.

Table 39: A compound of formula (I) wherein $R_1$ is sec-butyl, $R_2$ is methyl and $R_3$ is tert-butyl, and $X^-$ in each case corresponds to the anion of one of the acids mentioned in lines A.1 to A.153 of Table A.

Table 40: A compound of formula (I) wherein $R_1$ is sec-butyl, $R_2$ and $R_3$ are ethyl, and $X^-$ in each case corresponds to the anion of one of the acids mentioned in lines A.1 to A.153 of Table A.

Table 41: A compound of formula (I) wherein $R_1$ is sec-butyl, $R_2$ is methyl and $R_3$ is —CH$_2$—CH=CH$_2$, and $X^-$ in each case corresponds to the anion of one of the acids mentioned in lines A.1 to A.153 of Table A.

Table 42: A compound of formula (I) wherein $R_1$ is sec-butyl, $R_2$ is methyl and $R_3$ is —CH$_2$—C(=O)OC$_2$H$_5$, and $X^-$ in each case corresponds to the anion of one of the acids mentioned in lines A.1 to A.153 of Table A.

Table 43: A compound of formula (I) wherein $R_1$ is sec-butyl, $R_2$ is methyl and $R_3$ is benzyl, and $X^-$ in each case corresponds to the anion of one of the acids mentioned in lines. A.1 to A.153 of Table A.

Table 44: A compound of formula (I) wherein $R_1$ is sec-butyl, $R_2$ and $R_3$ together are —CH$_2$—CH$_2$—CH$_2$—, and $X^-$ in each case corresponds to the anion of one of the acids mentioned in lines A.1 to A.153 of Table A.

Table 45: A compound of formula (I) wherein $R_1$ is sec-butyl, $R_2$ and $R_3$ together are —CH$_2$—CH$_2$—CH$_2$—CH$_2$—, and $X^-$ in each case corresponds to the anion of one of the acids mentioned in lines A.1 to A.153 of Table A.

Table 46: A compound of formula (I) wherein $R_1$ is sec-butyl, $R_2$ is methyl and $R_3$ is —CH$_2$—CH$_2$—OH, and $X^-$ in each case corresponds to the anion of one of the acids mentioned in lines A.1 to A.153 of Table A.

Table 47: A compound of formula (I) wherein $R_1$ is sec-butyl, $R_2$ is methyl and $R_3$ is —CH$_2$—C(CH$_3$)OH, and $X^-$ in each case corresponds to the anion of one of the acids mentioned in lines A.1 to A.153 of Table A.

Table 48: A compound of formula (I) wherein $R_1$ is sec-butyl, $R_2$ is hydrogen and $R_3$ is ethyl, and $X^-$ in each case corresponds to the anion of one of the acids mentioned in lines A.1 to A.153 of Table A.

Table 49: A compound of formula (I) wherein $R_1$ is sec-butyl, $R_2$ is hydrogen and $R_3$ is —CH$_2$—CH=CH$_2$, and $X^-$ in each case corresponds to the anion of one of the acids mentioned in lines A.1 to A.153 of Table A.

Table 50: A compound of formula (I) wherein $R_1$ is sec-butyl, $R_2$ is hydrogen and $R_3$ is —CH$_2$—CH=CH, and $X^-$ in each case corresponds to the anion of one of the acids mentioned in lines A.1 to A.153 of Table A.

Table 51: A compound of formula (I) wherein $R_1$ is sec-butyl, $R_2$ is methyl and $R_3$ is —CH$_2$—CH≡CH, and $X^-$ in each case corresponds to the anion of one of the acids mentioned in lines A.1 to A.153 of Table A.

Table 52: A compound of formula (I) wherein $R_1$ is sec-butyl, $R_2$ is hydrogen and $R_3$ is isopropyl, and $X^-$ in each case corresponds to the anion of one of the acids mentioned in lines A.1 to A.153 of Table A.

Table 53: A compound of formula (I) wherein $R_1$ is sec-butyl, $R_2$ is hydrogen and $R_3$ is n-propyl, and $X^-$ in each case corresponds to the anion of one of the acids mentioned in lines A.1 to A.153 of Table A.

Table 54: A compound of formula (I) wherein $R_1$ is sec-butyl, $R_2$ is hydrogen and $R_3$ is n-butyl, and $X^-$ in each case corresponds to the anion of one of the acids mentioned in lines A.1 to A.153 of Table A.

Table 55: A compound of formula (I) wherein $R_1$ is sec-butyl, $R_2$ is hydrogen and $R_3$ is —CH$_2$—CH(CH$_3$)$_2$, and $X^-$ in each case corresponds to the anion of one of the acids mentioned in lines A.1 to A.153 of Table A.

Table 56: A compound of formula (I) wherein $R_1$ is sec-butyl, $R_2$ is hydrogen and $R_3$ is

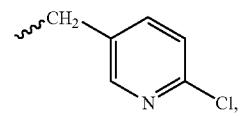

and $X^-$ in each case corresponds to the anion of one of the acids mentioned in lines A.1 to A.153 of Table A.

Table 57: A compound of formula (I) wherein $R_1$ is sec-butyl, $R_2$ is hydrogen and $R_3$ is

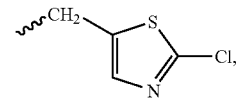

and $X^-$ in each case corresponds to the anion of one of the acids mentioned in lines A.1 to A.153 of Table A.

Table 58: A compound of formula (I) wherein $R_1$ is sec-butyl, $R_2$ is hydrogen and $R_3$ is —CH$_2$—C(=O)OC$_2$H$_5$, and $X^-$ in each case corresponds to the anion of one of the acids mentioned in lines A.1 to A.153 of Table A.

Table 59: A compound of formula (I) wherein $R_1$ is sec-butyl, $R_2$ is hydrogen and $R_3$ is —CH$_2$—C$_6$H$_4$—O—CF$_2$H, and $X^-$ in each case corresponds to the anion of one of the acids mentioned in lines A.1 to A.153 of Table A.

Table 60: A compound of formula (I) wherein $R_1$ is sec-butyl, $R_2$ is methyl and $R_3$ is —CH$_2$—CH=CH—C(=O)OCH$_2$C(=O)C$_6$H$_5$, and $X^-$ in each case corresponds to the anion of one of the acids mentioned in lines A.1 to A.153 of Table A.

Tables B and C below show experimentally determined percentage contents of C, H and N in compounds of formula (I) above. Since the compounds are mixtures of avermectin derivatives B1a and B1b wherein $R_1$ is isopropyl and sec-butyl, respectively, and the proportion thereof in the mixture is variable, the Tables do not give mathematically determined values for the contents of C, H and N.

TABLE B

Elemental analyses of compounds of formula

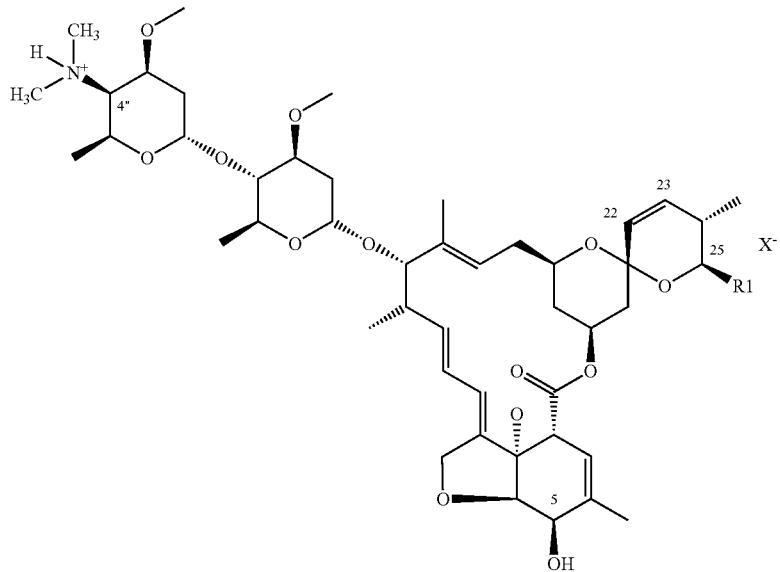

| No. | X—H | found content (%) C | H | N |
|---|---|---|---|---|
| B.1 | benzoic acid | 65.9 | 8.1 | 1.4 |
| B.2 | Maleic acid | 61.8 | 8.0 | 1.4 |
| B.3 | 2-hydroxybenzoic acid, salicyclic acid | 62.4 | 7.7 | 1.3 |
| B.4 | benzenesulfonic acid | 61.0 | 7.8 | 1.5 |
| B.5 | 2-ethylbutyric acid | 65.4 | 8.7 | 1.4 |
| B.6 | thiomalic acid | 60.1 | 7.9 | 1.3 |
| B.7 | 3,5-dihydroxy-benzoic acid | 62.3 | 7.9 | 1.3 |
| B.8 | trimesic acid | 61.2 | 7.5 | 1.2 |
| B.9 | D-(−)-quinic acid | 60.2 | 8.1 | 1.3 |
| B.10 | 2-bromo-benzoic acid | 60.4 | 7.4 | 1.2 |
| B.11 | 2-phenyl-benzoic acid | 68.3 | 8.0 | 1.2 |
| B.12 | 3,3'-thiodipropionic acid | 60.9 | 8.1 | 1.3 |
| B.13 | naphthalene-1-carboxylic acid | 67.6 | 7.9 | 1.2 |
| B.14 | 5-sulfosalicyclic acid | 59.4 | 7.6 | 1.3 |
| B.15 | 2-methoxy-phenylacetic acid | 65.1 | 8.2 | 1.2 |
| B.16 | benzene-1,2,4-tricarboxylic acid | 61.7 | 7.5 | 1.3 |
| B.17 | 3-hydroxy-benzoic acid | 64.0 | 7.7 | 1.3 |
| B.18 | D-gluconic acid | 56.8 | 7.9 | 1.1 |
| B.19 | 4,5-dichloro-phthalic acid | 60.0 | 7.2 | 1.3 |
| B.20 | n-octanoic acid (caprylic acid) | 65.9 | 8.9 | 1.3 |
| B.21 | 2,2'-dihydroxy-1,1'-dinaphthylmethane-3,3'-4,4'-methylene-bis(3-hydroxy-2-naphthoic acid) embonic acid | 64.7 | 7.5 | 1.2 |
| B.22 | 4-methoxy-phenylacetic acid (homoanisic acid) | 65.3 | 8.0 | 1.2 |
| B.23 | 2-anisic acid (2-methoxy-benzoic acid) | 65.0 | 7.9 | 1.2 |
| B.24 | adamantane-1-carboxylic acid | 67.3 | 8.7 | 1.2 |
| B.25 | pyridine-3,4-dicarboxylic acid | 62.8 | 8.2 | 2.9 |
| B.26 | 3,4-dihydroxy-benzoic acid | 62.0 | 7.5 | 1.2 |
| B.27 | 1-hydroxy-2-naphthoic acid (1-naphthol-2-carboxylic acid) | 66.5 | 8.1 | 1.2 |
| B.28 | 2,2'-oxydiacetic acid (diglycolic acid) | 60.3 | 8.2 | 1.4 |
| B.29 | O-ethyl-glycolic acid | 63.6 | 8.8 | 1.3 |
| B.30 | (2-naphthylthio)-acetic acid (S-(2-naphthyl)-thioglycolic acid) | 67.1 | 8.2 | 1.2 |
| B.31 | 2-naphthoxy-acetic acid | 67.6 | 8.3 | 1.1 |
| B.32 | p-toluic acid | 68.1 | 8.9 | 1.3 |
| B.33 | cyclohexanepropionic acid | 67.4 | 9.1 | 1.3 |
| B.34 | 3-methoxypropionic acid | 64.0 | 8.7 | 1.4 |
| B.35 | 3,4,5-trihydroxy-benzoic acid (gallic acid) | 61.7 | 8.0 | 1.3 |
| B.36 | pyromucic acid (furan-2-carboxylic acid) | 64.1 | 8.6 | 1.2 |
| B.37 | 2-methyl-benzoic acid (o-toluic acid) | 67.3 | 8.4 | 1.3 |
| B.38 | 3,6,9-trioxa-undecanedioic acid | 60.2 | 8.2 | 1.1 |
| B.39 | 3-(4-methoxyphenyl)-propionic acid (p-methoxy-hydrocinnamic acid) | 66.5 | 8.4 | 1.2 |
| B.40 | O-acetyl-salicyclic acid (aspirin) | 65.2 | 8.4 | 1.3 |

TABLE B-continued

Elemental analyses of compounds of formula

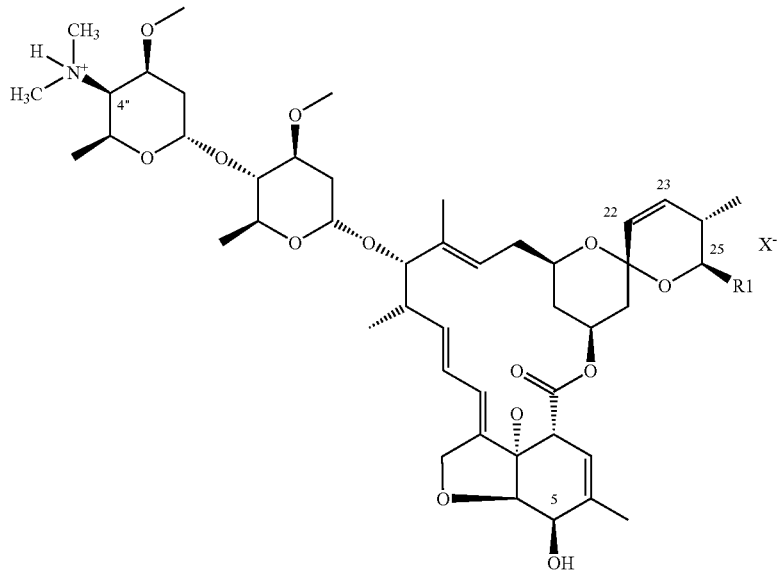

| No. | X—H | found content (%) C | H | N |
|---|---|---|---|---|
| B.41 | 3-fluoro-benzoic acid | 64.3 | 8.0 | 1.3 |
| B.42 | cyclohexanecarboxylic acid | 66.6 | 9.0 | 1.4 |
| B.43 | 5-chloro-2-hydroxy-benzoic acid (5-chloro-salicyclic acid) | 63.7 | 8.1 | 1.2 |
| B.44 | 2,5-dimethyl-benzoic acid (p-xylic acid) | 67.7 | 8.7 | 1.2 |
| B.45 | 3,4,5-trimethoxy-benzoic acid (trimethylgallic acid) | 65.9 | 8.6 | 1.2 |
| B.46 | 4-phenyl-butyric acid | 67.6 | 8.6 | 1.2 |
| B.47 | 3-trifluoromethyl-benzoic acid | 64.3 | 8.0 | 1.2 |
| B.48 | o-hydroxy-phenylacetic acid | 65.0 | 8.3 | 1.2 |
| B.49 | isophthalic acid | 63.7 | 7.9 | 1.1 |
| B.50 | 2,4,6-trihydroxy-benzoic acid | 63.2 | 8.2 | 1.1 |
| B.51 | trifluoromethanesulfonic acid | 66.6 | 8.9 | 1.4 |
| B.52 | 2-methyl-propionic acid (isobutyric acid) | 66.0 | 9.0 | 1.3 |
| B.53 | 2-thienylacetic acid (thiophene-2-acetic acid) | 65.2 | 8.4 | 1.2 |
| B.54 | 3,4-dimethoxy-benzoic acid (veratric acid) | 65.1 | 8.3 | 1.3 |
| B.55 | 2,2-bis(hydroxymethyl)-propionic acid | 64.9 | 8.9 | 1.2 |
| B.56 | 2-fluoro-phenylacetic acid | 66.4 | 8.4 | 1.3 |
| B.57 | 2-methyl-butyric acid | 66.2 | 9.0 | 1.4 |
| B.58 | hydroxy-acetic acid | 61.8 | 8.6 | 1.3 |
| B.59 | 4-chloro-phenylacetic acid | 65.3 | 8.3 | 1.1 |
| B.60 | 2-mercaptobenzoic acid (thiosalicyclic acid) | 63.3 | 8.1 | 1.2 |
| B.61 | (+/−)-2-hydroxyphenyl-acetic acid (DL-mandelic acid) | 63.1 | 8.0 | 1.1 |
| B.62 | 2,4-dihydroxypyrimidine-6-carboxylic acid | 55.4 | 7.9 | 3.1 |
| B.63 | toluene-4-sulfonic acid (p-toluene-sulfonic acid) | 61.9 | 8.3 | 1.2 |
| B.64 | 2-chloro-phenylacetic acid | 66.1 | 8.6 | 1.1 |
| B.65 | 2,4-dichloro-benzoic acid | 61.1 | 7.6 | 1.2 |
| B.66 | 2-mercapto-propionic acid (thiolactic acid) | 62.9 | 8.7 | 1.2 |
| B.67 | 2-chloro-benzoic acid | 63.3 | 7.8 | 1.1 |
| B.68 | methanesulfonic acid | 59.7 | 8.6 | 1.1 |
| B.69 | ethanesulfonic acid (ethyl-sulfuric acid) | 59.2 | 8.5 | 1.3 |
| B.70 | 4-phenoxy-butyric acid | 68.1 | 9.1 | 1.1 |
| B.71 | 4-tert-butyl-benzoic acid | 68.7 | 9.0 | 1.2 |
| B.72 | bis(2-carboxyethyl) disulfide | 59.1 | 8.0 | 1.1 |
| B.73 | pivalic acid (trimethylacetic acid) | 65.8 | 8.9 | 1.4 |
| B.74 | acrylic acid | 65.4 | 8.8 | 1.3 |
| B.75 | 3-benzoylpropionic acid (4-oxo-4-phenyl-butyric acid) | 67.7 | 8.8 | 1.1 |

TABLE B-continued

Elemental analyses of compounds of formula

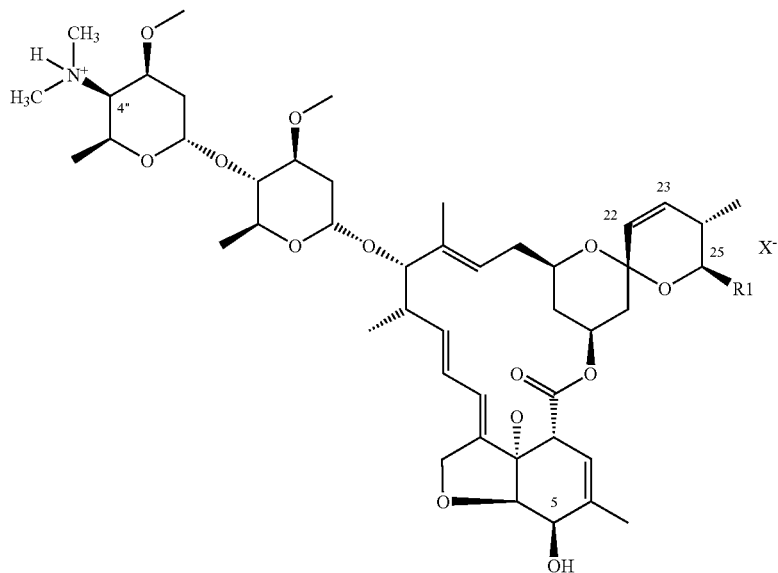

| No. | X—H | found content (%) | | |
|---|---|---|---|---|
| | | C | H | N |
| B.76 | (1R)-(−)-camphor-10-sulfonic acid hydrate | 63.4 | 8.7 | 1.1 |
| B.77 | 2-chloro-4-fluoro-benzoic acid | 62.3 | 7.9 | 1.2 |
| B.78 | 3,5-dimethoxy-benzoic acid | 66.1 | 8.5 | 1.2 |
| B.79 | 2-sulfobenzoic acid | 60.3 | 7.9 | 1.2 |
| B.80 | sulfoacetic acid | 59.6 | 8.3 | 1.3 |
| B.81 | 2-chloro-6-fluoro-benzoic acid | 61.7 | 7.9 | 1.3 |
| B.82 | 2,4-dihydroxy-benzoic acid | 62.6 | 8.2 | 1.3 |
| B.83 | methoxyacetic acid | 63.4 | 8.7 | 1.3 |
| B.84 | tartaric acid | 58.4 | 8.1 | 1.2 |
| B.85 | xanthene-9-carboxylic acid | 68.3 | 8.3 | 1.1 |
| B.86 | 4-pentenoic acid (allylacetic acid) | 66.1 | 8.9 | 1.4 |
| B.87 | vinylacetic acid | 64.9 | 8.6 | 1.3 |
| B.88 | 2-butynedioic acid (acetyldicarboxylic acid) | 61.8 | 8.3 | 1.4 |
| B.89 | 2-oxo-propionic acid (pyruvic acid) | 62.0 | 8.6 | 1.2 |
| B.90 | cyclohexylacetic acid | 66.6 | 9.0 | 1.3 |
| B.91 | 2-hydroxyisobutyric acid | 62.4 | 8.8 | 1.3 |
| B.92 | citric acid | 59.5 | 7.8 | 1.4 |
| B.93 | adipic acid | 61.1 | 8.1 | 1.2 |
| B.94 | sulfuric acid | 60.7 | 8.6 | 1.8 |
| B.95 | hydroxychloric acid | 59.7 | 8.4 | 1.4 |

TABLE C

Elemental analyses of compounds of formula

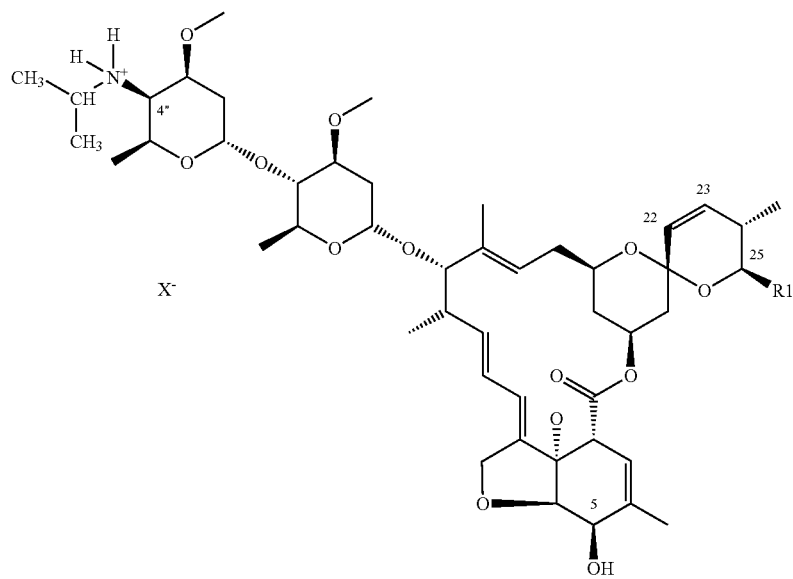

| No. | X—H | found content (%) | | |
|---|---|---|---|---|
| | | C | H | N |
| C.1 | benzoic acid | 66.3 | 8.2 | 1.5 |
| C.2 | maleic acid | 61.8 | 8.1 | 1.4 |
| C.3 | 2-hydroxybenzoic acid, salicyclic acid | 63.6 | 7.9 | 1.4 |
| C.4 | benzenesulfonic acid | 61.6 | 7.9 | 1.4 |
| C.5 | citric acid | 62.4 | 7.8 | 1.5 |

Formulation Examples for use in crop protection (%=percent by weight)

Example F1

| Emulsifiable concentrates | a) | b) | c) |
|---|---|---|---|
| active ingredient | 25% | 40% | 50% |
| calcium dodecylbenzenesulfonate | 5% | 8% | 6% |
| castor oil polyethylene glycol ether (36 mol EO) | 5% | — | — |
| tributylphenol polyethylene glycol ether (30 mol EO) | — | 12% | 4% |
| cyclohexanone | — | 15% | 20% |
| xylene mixture | 65% | 25% | 20% |

Mixing finely ground active ingredient and additives gives an emulsifiable concentrate which yields emulsions of the desired concentration on dilution with water.

Example F2

| Solutions | a) | b) | c) | d) |
|---|---|---|---|---|
| active ingredient | 80% | 10% | 5% | 95% |
| ethylene glycol monomethyl ether | 20% | — | — | — |
| polyethylene glycol (MW 400) | — | 70% | — | — |
| N-methylpyrrolid-2-one | — | 20% | — | — |
| epoxidised coconut oil | — | — | 1% | 5% |
| benzine (boiling range: 160-190°) | — | — | 94% | — |

Mixing finely ground active ingredient and additives gives a solution suitable for use in the form of microdrops.

Example F3

| Granules | a) | b) | c) | d) |
|---|---|---|---|---|
| active ingredient | 5% | 10% | 8% | 21% |
| kaolin | 94% | — | 79% | 54% |
| highly dispersed silicic acid | 1% | — | 13% | 7% |
| attapulgite | — | 90% | — | 18% |

The active ingredient is dissolved in dichloromethane, the solution is sprayed onto the carrier mixture and the solvent is evaporated off in vacuo.

Example F4

| Wettable powders | a) | b) | c) |
| --- | --- | --- | --- |
| active ingredient | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| octylphenol polyethylene glycol ether (7-8 mol EO) | — | 2% | — |
| highly dispersed silicic acid | 5% | 10% | 10% |
| kaolin | 62% | 27% | — |

Active ingredient and additives are mixed together and the mixture is ground in a suitable mill, yielding wettable powders that can be diluted with water to form suspensions of the desired concentration.

Example F5

| Emulsifiable concentrate | |
| --- | --- |
| active ingredient | 10% |
| octylphenol polyethylene glycol ether (4-5 mol EO) | 3% |
| calcium dodecylbenzenesulfonate | 3% |
| castor oil polyethylene glycol ether (36 mol EO) | 4% |
| cyclohexanone | 30% |
| xylene mixture | 50% |

Mixing finely ground active ingredient and additives gives an emulsifiable concentrate which yields emulsions of the desired concentration on dilution with water.

Example F6

| Extruder granules | |
| --- | --- |
| active ingredient | 10% |
| sodium lignosulfonate | 2% |
| carboxymethylcellulose | 1% |
| kaolin | 87% |

Active ingredient and additives are mixed together, the mixture is ground, moistened with water, extruded and granulated and the granules are dried in a stream of air.

Example F7

| Coated granules | |
| --- | --- |
| active ingredient | 3% |
| polyethylene glycol (MW 200) | 3% |
| kaolin | 94% |

Uniform application of the finely ground active ingredient to the kaolin moistened with polyethylene glycol in a mixer yields non-dusty coated granules.

Example F8

| Suspension concentrate | |
| --- | --- |
| active ingredient | 40% |
| ethylene glycol | 10% |
| nonylphenol polyethylene glycol ether (15 mol EO) | 6% |
| sodium lignosulfonate | 10% |
| carboxymethylcellulose | 1% |
| aqueous formaldehyde solution (37%) | 0.2% |
| aqueous silicone oil emulsion (75%) | 0.8% |
| water | 32% |

Mixing finely ground active ingredient and additives gives a suspension concentrate which yields suspensions of the desired concentration on dilution with water.

BIOLOGICAL EXAMPLES

Example B1

Action against *Spodoptera littoralis*

Young soybean plants are sprayed with an aqueous emulsion spray mixture comprising 12.5 ppm of test compound and, after the spray-coating has dried, the plants are populated with 10 caterpillars of *Spodoptera littoralis* in the first stage and then placed in a plastics container. 3 days later, the percentage reduction in population and the percentage reduction in feeding damage (% activity) are determined by comparing the number of dead caterpillars and the feeding damage on the treated plants with that on untreated plants.

Example B2

Action against *Spodoptera littoralis*, systemic:

Maize seedlings are placed in the test solution. 6 days later, the leaves are cut off, placed on moist filter paper in a petri dish and infested with 12 to 15 *Spodoptera littoralis* larvae in the $L_1$ stage. 4 days later, the percentage reduction in population (% activity) is determined by comparing the number of dead caterpillars on treated plants with that on untreated plants.

Example B3

Action Against *Heliothis virescens*

30-35 eggs of *Heliothis virescens*, from 0 to 24 hours old, are placed on filter paper in a petri dish on a layer of artificial nutrient. 0.8 ml of the test solution is then pipetted onto the filter papers. Evaluation is made 6 days later. The percentage reduction in population (% activity) is determined by comparing the number of dead eggs and larvae on treated plants with that on untreated plants.

Example B4

Action Against *Plutella xylostella* Caterpillars

Young cabbage plants are sprayed with an aqueous emulsion spray mixture comprising 12.5 ppm of test compound.

After the spray-coating has dried, the cabbage plants are populated with 10 caterpillars of *Plutella xylostella* in the first stage and placed in a plastics container. Evaluation is made 3 days later. The percentage reduction in population and the percentage reduction in feeding damage (% activity) are determined by comparing the number of dead caterpillars and the feeding damage on the treated plants with that on the untreated plants.

Example B5

Action Against *Frankliniella occidentalis*

Pieces of bean leaves are placed on agar in petri dishes and sprayed with test solution in a spray chamber. The leaves are then infested with a mixed population of *Frankliniella occidentalis*. Evaluation is made 10 days later. The percentage reduction (% activity) is determined by comparing the population on the treated leaves with that on untreated leaves.

Example B6

Action Against *Diabrotica balteata*

Maize seedlings are sprayed with an aqueous emulsion spray mixture comprising 12.5 ppm of the test compound and, after the spray-coating has dried, the maize seedlings are populated with 10 *Diabrotica balteata* larvae in the second stage and then placed in a plastics container. 6 days later, the percentage reduction in population (% activity) is determined by comparing the number of dead larvae on the treated plants with that on untreated plants.

Example B7

Action Against *Tetranychus urticae*

Young bean plants are populated with a mixed population of *Tetranychus urticae* and sprayed one day later with an aqueous emulsion spray mixture comprising 12.5 ppm of test compound. The plants are incubated for 6 days at 25° C. and subsequently evaluated. The percentage reduction in population (% activity) is determined by comparing the number of dead eggs, larvae and adults on the treated plants with that on untreated plants.

The compounds of the Tables exhibit a good action in the above tests B1 to B7. For example, especially compounds B.1 to B.4, B.11, B.22, B.29, B.32, B.36, B.41, B.44, B.47, B.51, B.52, B.60, B.70, B.71, B.74, B.82, B.83, B.84, B.86, B.91, B.92 and B.94 bring about a reduction in the pest population mentioned in these tests of more than 80%.

The invention claimed is:
1. A compound of formula

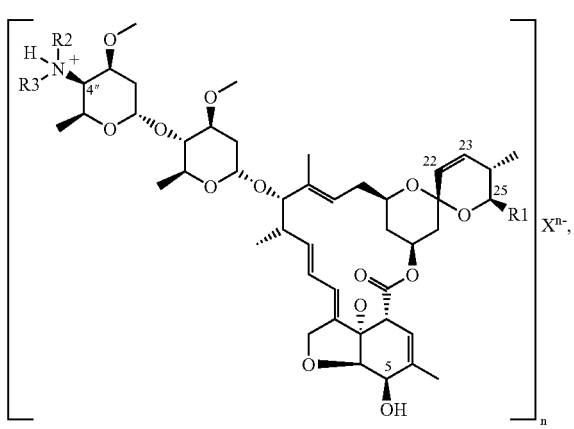

(I)

wherein $X^-$ is an anion;
n is 1, 2, 3 or 4;
$R_1$ is $C_1$-$C_{12}$ alkyl, $C_3$-$C_8$cycloalkyl; or $C_2$-$C_{12}$alkenyl;
$R_2$ is mono- to penta-substituted $C_1$-$C_{12}$alkyl, unsubstituted or mono- to penta-substituted $C_2$-$C_{12}$alkenyl;
$R_3$ is mono- to penta-substituted $C_1$-$C_{12}$alkyl, unsubstituted or mono- to penta-substituted $C_3$-$C_{12}$cycloalkyl, unsubstituted or mono- to penta-substituted $C_2$-$C_{12}$alkenyl; unsubstituted or mono- to penta-substituted $C_2$-$C_{12}$alkynyl; or $R_2$ and $R_3$ together are a three- to seven-membered alkylene bridge, or a four- to seven-membered alkenylene bridge wherein a —$CH_2$— group may have been replaced by O, S or $NR_4$;
wherein the substituents of the mono- to penta-substituted $C_1$-$C_{12}$alkyl, unsubstituted or mono- to penta-substituted $C_3$-$C_{12}$cycloalkyl, unsubstituted or mono- to penta-substituted $C_2$-$C_{12}$alkenyl, unsubstituted or mono- to penta-substituted $C_2$-$C_{12}$alkynyl are selected from the group consisting of OH, halogen, halo-$C_1$-$C_2$alkyl, CN, $NO_2$, $C_2$-$C_6$alkynyl, $C_3$-$C_8$cycloalkyl, norbornylenyl, $C_3$-$C_8$cycloalkenyl, $C_3$-$C_8$cycloalkenyl unsubstituted or substituted by from one to three methyl groups, $C_3$-$C_8$halocycloalkyl, $C_1$-$C_{12}$alkoxy, $C_1$-$C_6$alkoxy-$C_1$-$C_6$alkyl, $C_3$-$C_8$cycloalkoxy, $C_1$-$C_{12}$haloalkoxy, $C_1$-$C_{12}$alkylthio, $C_3$-$C_8$cycloalkylthio, $C_1$-$C_{12}$haloalkylthio, $C_1$-$C_{12}$alkylsulfinyl, $C_3$-$C_8$cycloalkylsulfinyl, $C_1$-$C_{12}$haloalkylsulfinyl, $C_3$-$C_8$halocycloalkylsulfinyl, $C_1$-$C_{12}$alkylsulfonyl, $C_3$-$C_8$cycloalkylsulfonyl, $C_1$-$C_{12}$haloalkylsulfonyl, $C_3$-$C_8$halocycloalkylsulfonyl, $C_2$-$C_8$alkenyl, $C_2$-$C_8$alkynyl, $NH(C_1$-$C_6$alkyl), $N(C_1$-$C_6$alkyl)$_2$, —C(=O)$R_5$, —NHC(=O)$R_6$, —P(=O)(O$C_1$-$C_6$alkyl)$_2$, aryl, heterocyclyl, aryloxy, heterocyclyloxy; and also aryl, heterocyclyl, aryloxy and heterocyclyloxy that, depending upon the possibilities of substitution at the ring, are mono- to penta-substituted by substituents selected from the group consisting of OH, halogen, CN, $NO_2$, $C_1$-$C_{12}$alkyl, $C_3$-$C_8$cycloalkyl, $C_1$-$C_{12}$haloalkyl, $C_1$-$C_{12}$alkoxy, $C_1$-$C_{12}$haloalkoxy, $C_1$-$C_{12}$alkylthio, $C_1$-$C_{12}$haloalkylthio, $C_1$-$C_6$alkoxy-$C_1$-$C_6$alkyl, dimethylamino-$C_1$-$C_6$alkoxy, $C_2$-$C_8$alkenyl, $C_2$-$C_8$alkynyl, phenoxy, phenyl-$C_1$-$C_6$alkyl; phenoxy unsubstituted or substituted by from one to three substituents selected independently of one another from halogen, methoxy, trifluoromethyl and trifluoromethoxy; phenyl-$C_1$-$C_6$alkoxy unsubstituted or substituted in the aromatic ring by from one to three substituents selected independently of one another from halogen, methoxy, trifluoromethyl and trifluoromethoxy; phenyl-$C_2$-$C_6$alkenyl, phenyl-$C_2$-$C_6$alkynyl, methylenedioxy, —C(=O)$R_5$, —O—C(=O)$R_6$, —NH—C(=O)$R_6$, $NH_2$, $NH(C_1$-$C_{12}$alkyl), $N(C_1$-$C_{12}$alkyl)$_2$, $C_1$-$C_6$alkylsulfinyl, $C_3$-$C_8$cycloalkylsulfinyl, $C_1$-$C_6$haloalkylsulfinyl, $C_3$-$C_8$halocycloalkylsulfinyl, $C_1$-$C_6$alkylsulfonyl, $C_3$-$C_8$cycloalkylsulfonyl, $C_1$-$C_6$haloalkylsulfonyl and $C_3$-$C_8$halocycloalkylsulfonyl;
$R_4$ is $C_1$-$C_8$alkyl, $C_3$-$C_8$cycloalkyl, $C_2$-$C_8$alkenyl, $C_2$-$C_8$alkynyl, benzyl or —C(=O)—$R_5$;
$R_5$ is H, OH, SH, $NH_2$, $NH(C_1$-$C_{12}$alkyl), $N(C_1$-$C_{12}$alkyl)$_2$, $C_1$-$C_{12}$alkyl, $C_1$-$C_{12}$haloalkyl, $C_1$-$C_{12}$alkoxy, $C_1$-$C_{12}$haloalkoxy, $C_1$-$C_6$alkoxy-$C_1$-$C_6$alkoxy, $C_1$-$C_{12}$alkylthio, $C_2$-$C_8$alkenyloxy, $C_2$-$C_8$alkynyloxy; phenyl, phenoxy, benzyloxy, —NH-phenyl, —N($C_1$-$C_6$alkyl)-phenyl, NH—$C_1$-$C_6$alkyl-C(=O)—$R_7$, —N($C_1$-$C_6$alkyl)-$C_1$-$C_6$alkyl-C(=O)—$R_7$; or phenyl, phenoxy, benzyloxy, NH-phenyl or —N($C_1$-$C_6$alkyl)-phenyl substituted in the aromatic ring by from one to three substituents selected independently of one another from halogen, $C_1$-$C_6$alkoxy, $C_1$-$C_6$haloalkyl and $C_1$-$C_6$haloalkoxy;

$R_6$ is H, $C_1$-$C_{12}$alkyl, $C_1$-$C_{12}$haloalkyl, $C_2$-$C_8$alkenyl, $C_2$-$C_8$alkynyl, phenyl, benzyl, $NH_2$, NH($C_1$-$C_{12}$alkyl), N($C_1$-$C_{12}$alkyl)$_2$, —NH-phenyl or —N($C_1$-$C_{12}$alkyl)-phenyl; and $R_7$ is H, OH, $C_1$-$C_{12}$alkyl, $C_1$-$C_{12}$alkoxy, $C_1$-$C_6$alkoxy-$C_1$-$C_6$alkoxy, $C_2$-$C_8$alkenyloxy, phenyl, phenoxy, benzyloxy, $NH_2$, NH($C_1$-$C_{12}$alkyl), N($C_1$-$C_{12}$alkyl)$_2$, —NH-phenyl or —N($C_1$-$C_{12}$alkyl)-phenyl; and, where applicable, an E/Z isomer, E/Z isomeric mixture and/or tautomer thereof.

2. A compound according to claim 1 of formula (I) wherein $R_1$ is isopropyl or sec-butyl.

3. A pesticidal composition comprising as active ingredient at least one compound according to claim 1 of formula (I), in agrochemically acceptable salt form, and at least one adjuvant.

4. A method of controlling pests, which comprises applying a composition according to claim 3 to the pests or to the locus thereof.

5. A process for the preparation of a composition according to claim 3 comprising at least one adjuvant, which comprises intimately mixing and/or grinding the active ingredient with the adjuvant(s).

6. A method according to claim 4 for the protection of plant propagation material, which comprises treating the propagation material or the planting site of the propagation material.

7. Plant propagation material treated in accordance with the method described in claim 6.

* * * * *